US011317976B2

(12) United States Patent
Johnson et al.

(10) Patent No.: US 11,317,976 B2
(45) Date of Patent: May 3, 2022

(54) ARTICULABLE WRIST WITH FLEXIBLE MEMBER AND ROLLER SUPPORTS

(71) Applicant: Ethicon LLC, Guaynabo, PR (US)

(72) Inventors: Eric N. Johnson, Maineville, OH (US); Mark Allen Davison, Maineville, OH (US); Tyler N. Brehm, Dayton, OH (US)

(73) Assignee: Ethicon LLC, Guaynabo, PR (US)

( * ) Notice: Subject to any disclaimer, the term of this patent is extended or adjusted under 35 U.S.C. 154(b) by 171 days.

(21) Appl. No.: 16/549,175

(22) Filed: Aug. 23, 2019

(65) Prior Publication Data

US 2021/0052333 A1 Feb. 25, 2021

(51) Int. Cl.
| | |
|---|---|
| *A61B 17/29* | (2006.01) |
| *A61B 34/30* | (2016.01) |
| *A61B 34/00* | (2016.01) |
| *A61B 17/00* | (2006.01) |

(52) U.S. Cl.
CPC ........ *A61B 34/30* (2016.02); *A61B 17/00234* (2013.01); *A61B 17/2909* (2013.01); *A61B 34/71* (2016.02); *A61B 2017/00477* (2013.01); *A61B 2017/2926* (2013.01); *A61B 2034/301* (2016.02); *A61B 2034/305* (2016.02); *A61B 2034/715* (2016.02)

(58) Field of Classification Search
CPC ... A61B 17/00; A61B 17/29; A61B 17/00234; A61B 17/2909; A61B 2017/292; A61B 2017/2926; A61B 2017/00477; A61B 2034/305; A61B 2034/715; A61B 34/00; A61B 34/30
See application file for complete search history.

(56) References Cited

U.S. PATENT DOCUMENTS

| | | | |
|---|---|---|---|
| 2009/0299143 A1 | 12/2009 | Conlon | |
| 2016/0184552 A1* | 6/2016 | Hou | A61M 25/0113 |
| | | | 604/95.01 |
| 2017/0165009 A1 | 6/2017 | Chaplin | |

FOREIGN PATENT DOCUMENTS

| | | |
|---|---|---|
| WO | 2012078951 A1 | 6/2012 |
| WO | 2014151952 A1 | 9/2014 |

OTHER PUBLICATIONS

ISR-WO from application PCT/IB2020/057729 dated Nov. 5, 2020 and that claims priority to the present US application.

* cited by examiner

*Primary Examiner* — Vi X Nguyen
(74) *Attorney, Agent, or Firm* — Vorys, Sater, Seymour and Pease LLP

(57) ABSTRACT

An articulable wrist for an end effector includes a first linkage rotatably coupled to a second linkage at a first articulation joint, a flexible member extending at least partially through a central channel cooperatively defined by the first and second linkages, and a first pair of roller supports arranged at the first articulation joint and laterally offset from each other, each roller support extending parallel to a first pivot axis extending through the first articulation joint. A drive cable extends through a first axially-extending conduit defined in the flexible member and through a gap defined between the first pair of roller supports. The drive cable is supported at the first articulation joint by the first pair of roller supports during articulation and the first pair of roller supports prevents a centerline of the drive cable from moving past the first pivot axis during actuation of the end effector.

20 Claims, 9 Drawing Sheets

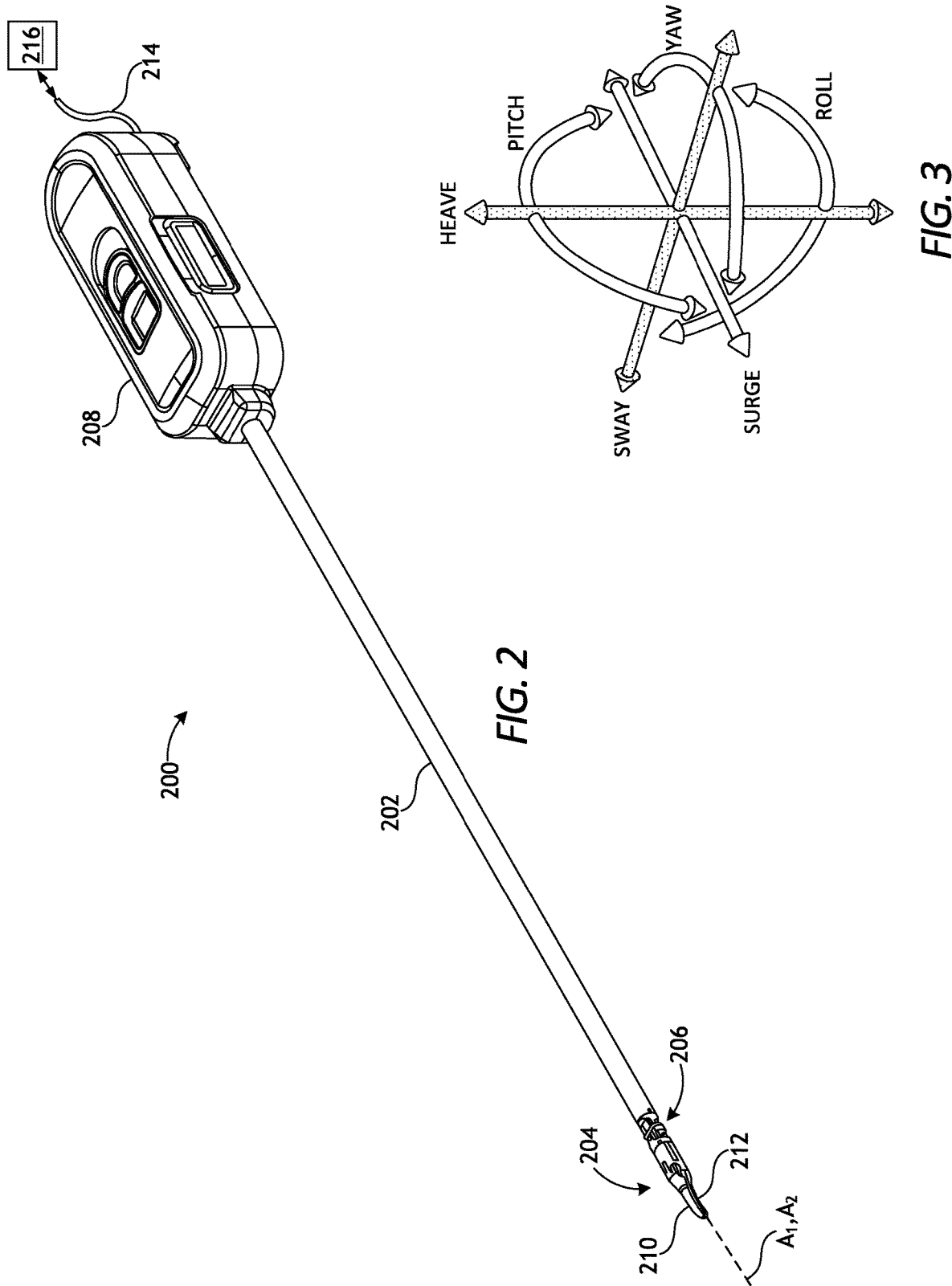

ARTICULABLE WRIST WITH FLEXIBLE MEMBER AND ROLLER SUPPORTS

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The instruments and tools introduced into the abdominal cavity via the trocar can be used to engage and/or treat tissue in a number of ways to achieve a diagnostic or therapeutic effect.

Various robotic systems have recently been developed to assist in MIS procedures. Robotic systems can allow for more instinctive hand movements by maintaining natural eye-hand axis. Robotic systems can also allow for more degrees of freedom in movement by including an articulable "wrist" joint that creates a more natural hand-like articulation. In such systems, an end effector positioned at the distal end of the instrument can be articulated (moved) using a cable driven motion system having one or more drive cables (or other elongate members) that extend through the wrist joint. A user (e.g., a surgeon) is able to remotely operate the end effector by grasping and manipulating in space one or more controllers that communicate with a tool driver coupled to the surgical instrument. User inputs are processed by a computer system incorporated into the robotic surgical system, and the tool driver responds by actuating the cable driven motion system and thereby actively controlling the tension balance in the drive cables. Moving the drive cables articulates the end effector to desired angular positions and configurations.

In articulated robotic tools, cables that actuate jaw opening, closing, and clamping are routed through the wrist and articulation joints to reach the end effector. To help guide the position of the cables through the pitch and yaw articulation joints of the wrist, the cables can be further routed through a flexible member that also extends through the wrist. The flexible member is often referred to as a "multilumen" since it defines a plurality of axially-extending cable pathways or conduits that accommodate the various cables.

The cables extending through the flexible member and articulation joints of the wrist are not typically constrained to be on the centerline axis at the articulation pivots. Consequently, as the articulation joint angle moves away from the straight position during actuation, the cable pathways through the flexible member can dip above or below the pivot axis governed by the stiffness of the flexible member and its ability to flex in response to the clamping load. As cables tighten under tensile loading, such as when a high closure force is applied to a closure cable to "clamp" the jaws on tissue, they will tend to find the shortest path through the articulation pivots, which may cause the cables to dip below the pivot axis. If a cable dips below the pivot axis, this can create an unbalanced moment that causes the jaws to move abruptly (i.e., dive) in the direction of the imbalance. This unexpected tip deflection or "tip dive" is undesirable in surgical use where the jaws are clamping critical structures.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIG. 2 is an isometric side view of an example surgical tool that may incorporate some or all of the principles of the present disclosure.

FIG. 3 illustrates potential degrees of freedom in which the wrist of the surgical tool of FIG. 2 may be able to articulate (pivot) or translate.

DETAILED DESCRIPTION

The present disclosure is related to robotic surgical systems and, more particularly, to end effectors with articulable wrists that include a flexible member extending through the articulable wrists and roller supports used to help prevent closure and open cables from migrating past corresponding pivot axes during articulation.

In cable articulated robotic tools, undesirable motion of the jaw tip can result when a high closure force is applied to "clamp" the jaw on tissue in a surgical procedure. This jaw tip motion is generated by slight off center positional offsets of the closure cable in the articulation joints at certain poses. This creates an unbalancing moment which caused the jaw to move abruptly (dive) in the direction of the imbalance. This "tip dive" is unexpected and undesirable in surgical use where the jaw is clamping critical structures. Simulation studies have shown that the end effector will move in the direction of articulation if the centerline of the closure cable falls below the articulation pivot axis due to flexure of an unsupported flexible member at the articulation joint.

Embodiments described herein disclose an articulable wrist for an end effector of a surgical tool. The articulable wrist includes a first linkage rotatably coupled to a second linkage at a first articulation joint, a flexible member extending at least partially through a central channel cooperatively defined by the first and second linkages, and a first pair of roller supports arranged at the first articulation joint and laterally offset from each other. Each roller support extends parallel to a first pivot axis extending through the first articulation joint. A closure cable extends through a first axially-extending conduit defined in the flexible member and through a gap defined between the first pair of roller supports. The closure cable may be supported at the first articulation joint by the first pair of roller supports during articulation, and the first pair of roller supports may help prevent a centerline of the closure cable from moving past the first pivot axis during actuation of the end effector Accordingly, embodiments of the present disclosure employ roller supports operable to prevent the closure cable from deviating below the pivot axis during closure because it is captured by the roller supports. This will reduce the offset moment created when tension on the closure cable is increased during jaw clamping. This constraint may also reduce the effect of undesirable end effector motion ("tip dive"). The roller supports can be present in both the pitch and yaw articulation joints.

Figure 1:
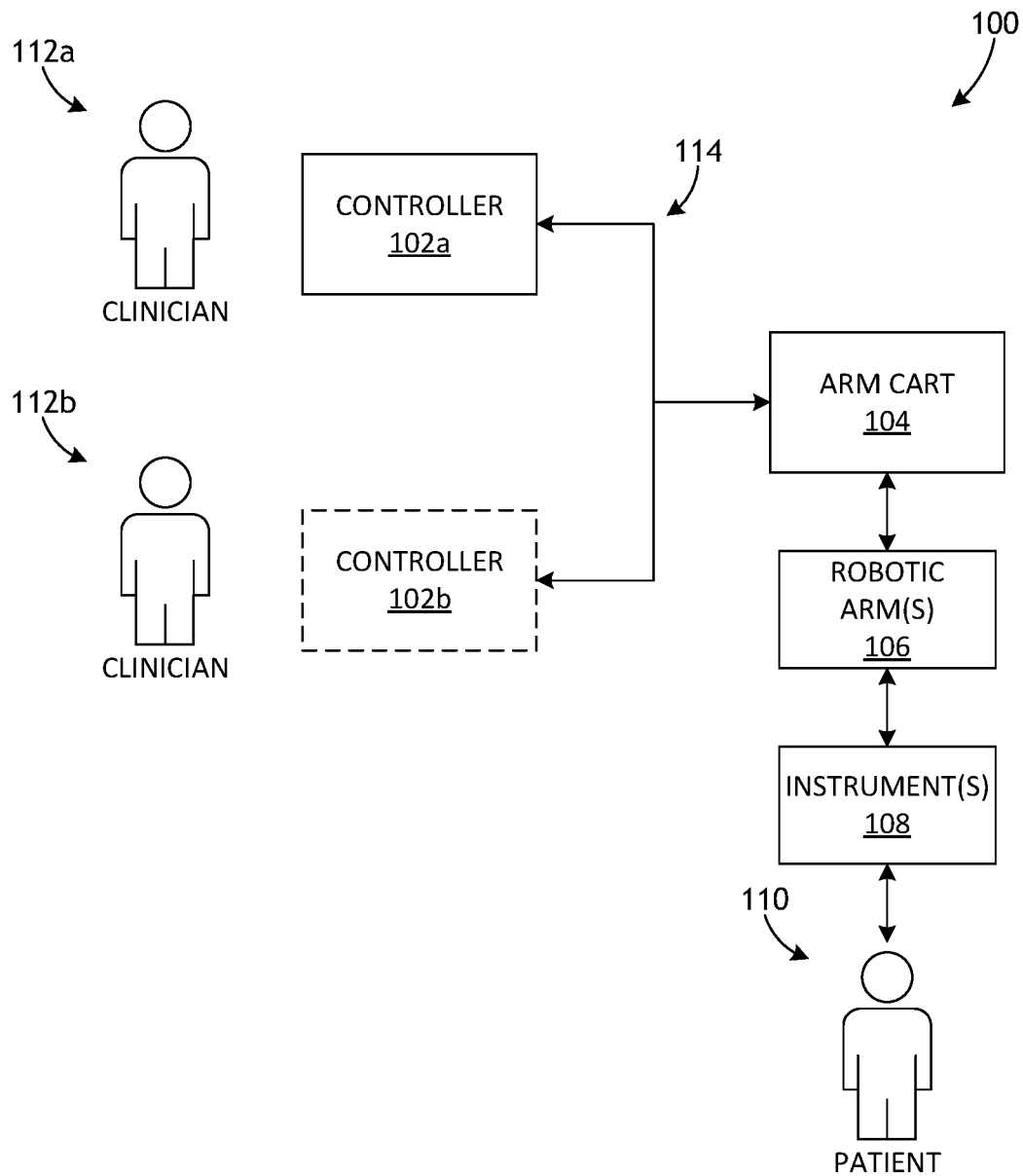
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one set of user input controllers 102a and at least one control computer 104. The control computer 104 may be mechanically and/or electrically coupled to a robotic manipulator and, more particularly, to one or more robotic arms 106 (alternately referred to as "tool drivers"). In some embodiments, the robotic manipulator may be included in or otherwise mounted to an arm cart capable of making the system portable. Each robotic arm 106 may include and otherwise provide a location for mounting one or more surgical instruments or tools 108 for performing various surgical tasks on a patient 110. Operation of the robotic arms 106 and associated tools 108 may be directed by a clinician 112a (e.g., a surgeon) from the user input controller 102a.

In some embodiments, a second set of user input controllers 102b (shown in dashed lines) may be operated by a second clinician 112b to direct operation of the robotic arms 106 and tools 108 in conjunction with the first clinician 112a. In such embodiments, for example, each clinician 112a,b may control different robotic arms 106 or, in some cases, complete control of the robotic arms 106 may be passed between the clinicians 112a,b. In some embodiments, additional robotic manipulators (not shown) having additional robotic arms (not shown) may be utilized during surgery on the patient 110, and these additional robotic arms may be controlled by one or more of the user input controllers 102a,b.

The control computer 104 and the user input controllers 102a,b may be in communication with one another via a communications link 114, which may be any type of wired or wireless telecommunications means configured to carry a variety of communication signals (e.g., electrical, optical, infrared, etc.) and according to any communications protocol.

The user input controllers 102a,b generally include one or more physical controllers that can be grasped by the clinician 112a,b and manipulated in space while viewing the procedure via a stereo display. The physical controllers generally comprise manual input devices movable in multiple degrees of freedom, and often include an actuatable handle or pedal for actuating the surgical tool(s) 108. The control computer 104 can also include an optional feedback meter viewable by the clinician 112a,b via a display to provide a visual indication of various surgical instrument metrics, such as the amount of force being applied to the surgical instrument (i.e., a cutting instrument or dynamic clamping member).

FIG. 2 is an isometric side view of an example surgical tool 200 that may incorporate some or all of the principles of the present disclosure. The surgical tool 200 may be the same as or similar to the surgical tool(s) 108 of FIG. 1 and, therefore, may be used in conjunction with a robotic surgical system, such as the robotic surgical system 100 of FIG. 1. In other embodiments, however, aspects of the surgical tool 200 may be adapted for use in a manual or hand-operated manner, without departing from the scope of the disclosure.

As illustrated, the surgical tool 200 includes an elongated shaft 202, an end effector 204, a wrist 206 (alternately referred to as a "wrist joint" or an "articulable wrist joint") that couples the end effector 204 to the distal end of the shaft 202, and a drive housing 208 coupled to the proximal end of the shaft 202. In robotic surgical systems, the drive housing 208 can include coupling features that releasably couple the surgical tool 200 to a robotic surgical system (e.g., the robotic arm 106 of FIG. 1).

The terms "proximal" and "distal" are defined herein relative to a robotic surgical system having an interface configured to mechanically and electrically couple the surgical tool 200 (e.g., the drive housing 208) to a robotic manipulator. The term "proximal" refers to the position of an element closer to the robotic manipulator and the term "distal" refers to the position of an element closer to the end effector 204 and thus further away from the robotic manipulator. Alternatively, in manual or hand-operated applications, the terms "proximal" and "distal" are defined herein relative to a user, such as a surgeon or clinician. The term "proximal" refers to the position of an element closer to the user and the term "distal" refers to the position of an element closer to the end effector 204 and thus further away from the user. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 200, the end effector 204 is configured to move (pivot) relative to the shaft 202 at the wrist 206 to position the end effector 204 at desired orientations and locations relative to a surgical site. To accomplish this, the drive housing 208 includes (contains) various drive inputs and mechanisms (e.g., gears, actuators, etc.) designed to control operation of various features associated with the end effector 204 (e.g., clamping, firing, rotation, articulation, cutting, etc.). In at least some applications, the shaft 202, and hence the end effector 204 coupled thereto, is configured to rotate about a longitudinal axis $A_1$ of the shaft 202. In such embodiments, at least one of the drive inputs controls rotational movement of the shaft 202 about the longitudinal axis $A_1$.

The surgical tool 200 may include, but is not limited to, forceps, a grasper, a needle driver, scissors, an electro cautery tool, a vessel sealer, a stapler, a clip applier, a hook, a spatula, a suction tool, an irrigation tool, an imaging device (e.g., an endoscope or ultrasonic probe), or any combination thereof. In some embodiments, the surgical tool 200 may also be configured to apply energy to tissue, such as radio frequency (RF) energy. In the illustrated embodiment, the end effector 204 comprises a tissue grasper and vessel sealer that includes opposing jaws 210, 212 configured to move (articulate) between open and closed positions. As will be appreciated, however, the opposing jaws 210, 212 may alternatively form part of other types of end effectors such as, but not limited to, surgical scissors, a clip applier, a needle driver, a babcock including a pair of opposed grasping jaws, bipolar jaws (e.g., bipolar Maryland grasper, forceps, a fenestrated grasper, etc.), etc. One or both of the jaws 210, 212 may be configured to pivot relative to the other to open and close the jaws 210, 212. The principles of the present disclosure, however, are equally applicable to end effectors without opposing jaws.

FIG. 3 illustrates the potential degrees of freedom in which the wrist 206 may be able to articulate (pivot). The wrist 206 comprises a joint configured to allow pivoting movement of the end effector 204 relative to the shaft 202. The degrees of freedom of the wrist 206 are represented by three translational variables (i.e., surge, heave, and sway) and three rotational variables (i.e., Euler angles or roll, pitch, and yaw). The translational and rotational variables describe the position and orientation of the end effector 204 with respect to a given reference Cartesian frame. "Surge" refers to forward and backward translational movement, "heave" refers to translational movement up and down, and "sway" refers to translational movement left and right. "Roll" refers to tilting side to side, "pitch" refers to tilting forward and backward, and "yaw" refers to turning left and right.

The pivoting motion can include pitch movement about a first axis of the wrist 206 (e.g., X-axis), yaw movement about a second axis of the wrist 206 (e.g., Y-axis), and combinations thereof to allow for 360° rotational movement of the end effector 204 about the wrist 206. In other applications, the pivoting motion can be limited to movement in a single plane, e.g., only pitch movement about the first axis of the wrist 206 or only yaw movement about the second axis of the wrist 206, such that the end effector 204 moves only in a single plane.

Referring again to FIG. 2, the surgical tool 200 may also include a plurality of drive cables (obscured in FIG. 2) that form part of a cable driven motion system that facilitates movement and articulation of the end effector 204 relative to the shaft 202. Moving (actuating) the drive cables moves the end effector 204 between an unarticulated position and an articulated position. The end effector 204 is depicted in FIG. 2 in the unarticulated position where a longitudinal axis $A_2$ of the end effector 204 is substantially aligned with the longitudinal axis $A_1$ of the shaft 202, such that the end effector 204 is at a substantially zero angle relative to the shaft 202. In the articulated position, the longitudinal axes $A_1$, $A_2$ would be angularly offset from each other such that the end effector 204 is at a non-zero angle relative to the shaft 202.

In some embodiments, the surgical tool 200 may be supplied with electrical power (current) via a power cable 214 coupled to the drive housing 208. In other embodiments, the power cable 214 may be omitted and electrical power may be supplied to the surgical tool 200 via an internal power source, such as one or more batteries or fuel cells. In such embodiments, the surgical tool 200 may alternatively be characterized and otherwise referred to as an "electrosurgical instrument" capable of providing electrical energy to the end effector 204. The power cable 214 may place the surgical tool 200 in communication with a generator 216 that supplies energy, such as electrical energy (e.g., radio frequency energy), ultrasonic energy, microwave energy, heat energy, or any combination thereof, to the surgical tool 200 and, more particularly, to the end effector 204.

Figure 4:
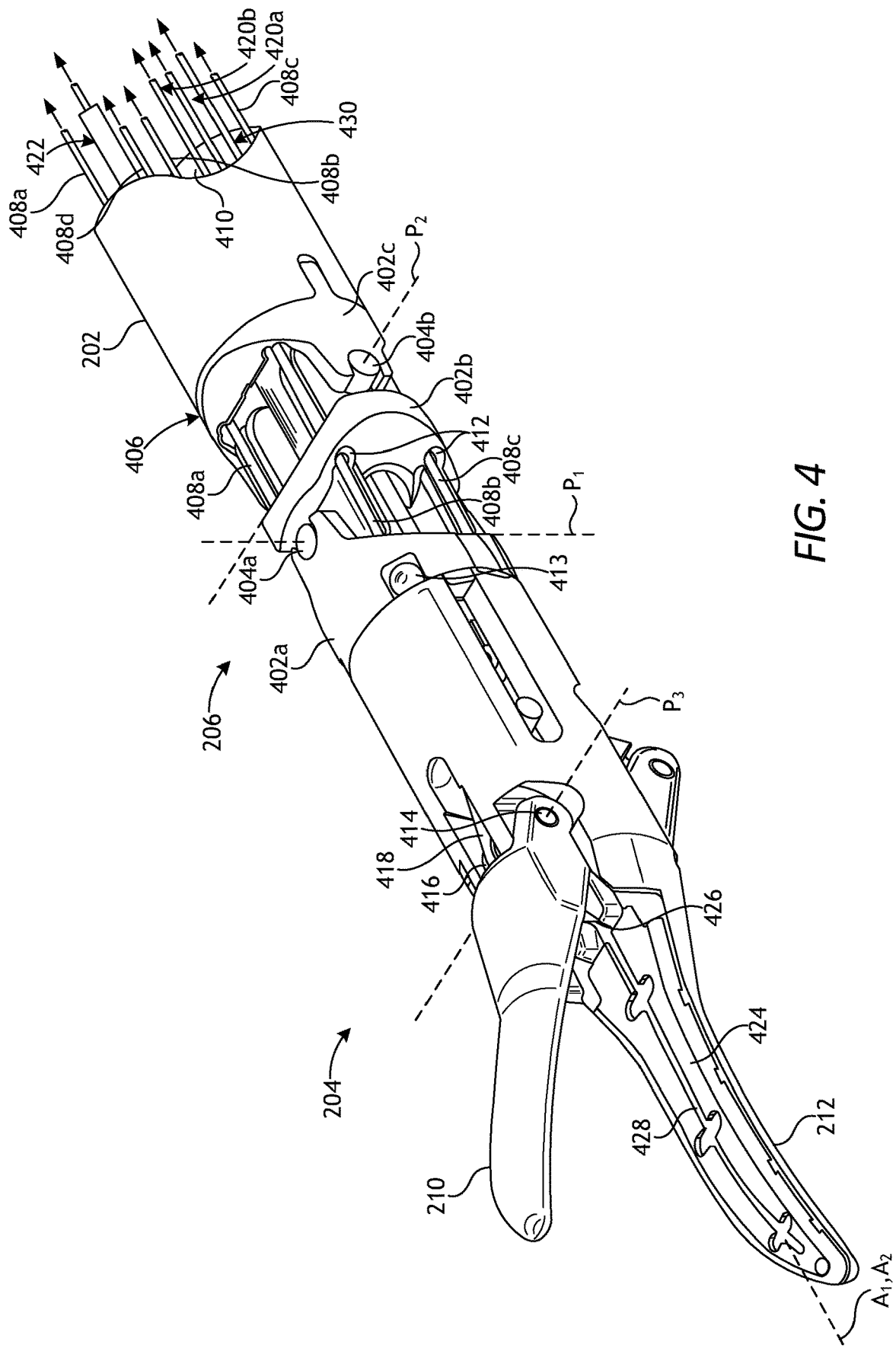
FIG. 4 is an enlarged isometric view of the distal end of the surgical tool of FIG. 2.

FIG. 4 is an enlarged isometric view of the distal end of the surgical tool 200 of FIG. 2. More specifically, FIG. 4 depicts an enlarged view of the end effector 204 and the wrist 206, with the jaws 210, 212 of the end effector 204 in the open position. The wrist 206 operatively couples the end effector 204 to the shaft 202. In some embodiments, however, a shaft adapter may be directly coupled to the wrist 206 and otherwise interpose the shaft 202 and the wrist 206. Accordingly, the wrist 206 may be operatively coupled to the shaft 202 either through a direct coupling engagement where the wrist 206 is directly coupled to the distal end of the shaft 202, or an indirect coupling engagement where a shaft adapter interposes the wrist 206 and the distal end of the shaft 202. As used herein, the term "operatively couple" refers to a direct or indirect coupling engagement between two components.

To operatively couple the end effector 204 to the shaft 202, the wrist 206 includes a first or "distal" linkage 402a, a second or "intermediate" linkage 402b, and a third or "proximal" linkage 402c. The linkages 402a-c facilitate articulation of the wrist 206 relative to the elongate shaft 202. Articulation via the linkages 402a-c may be limited to pitch only, yaw only, or a combination of pitch and yaw. As illustrated, the distal end of the distal linkage 402a may be coupled to the end effector 204 and, more particularly, to the lower jaw 212 (or an extension of the lower jaw 212). The proximal end of the distal linkage 402a may be rotatably coupled to the intermediate linkage 402b at a first axle 404a, and the intermediate linkage 402b may also be rotatably coupled to the proximal linkage 402c at a second axle 404b. The proximal end of the proximal linkage 402c may be coupled to a distal end 406 of the shaft 202 (or alternatively a shaft adapter).

A first pivot axis $P_1$ extends through the first axle 404a and a second pivot axis $P_2$ extends through the second axle 404b. The first pivot axis $P_1$ is substantially perpendicular (orthogonal) to the longitudinal axis $A_2$ of the end effector 204, and the second pivot axis $P_2$ is substantially perpendicular (orthogonal) to both the longitudinal axis $A_2$ and the first pivot axis $P_1$. Movement about the first pivot axis $P_1$ provides "yaw" articulation of the wrist 206, and movement about the second pivot axis $P_2$ provides "pitch" articulation of the wrist 206. Alternatively, the first pivot axis $P_1$ could be configured to provide "pitch" articulation and the second pivot axis $P_2$ could be configured to provide "yaw" articulation.

A plurality of drive cables, shown as drive cables 408a, 408b, 408c, and 408d, extend longitudinally within a lumen 410 defined by the shaft 202 (or a shaft adaptor) and pass through the wrist 206 to be operatively coupled to the end effector 204. The drive cables 408a-d form part of the cable driven motion system briefly described above, and may be referred to and otherwise characterized as cables, bands, lines, cords, wires, woven wires, ropes, strings, twisted strings, elongate members, etc. The drive cables 408a-d can be made from a variety of materials including, but not limited to, metal (e.g., tungsten, stainless steel, etc.) a polymer (e.g., ultra-high molecular weight polyethylene), a synthetic fiber (e.g., KEVLAR®, VECTRAN®, etc.), or any combination thereof. While four drive cables 408a-d are depicted in FIG. 4, more or less than four drive cables 408a-d may be included, without departing from the scope of the disclosure.

The drive cables 408a-d extend proximally from the end effector 204 to the drive housing 208 (FIG. 2) where they are operatively coupled to various actuation mechanisms (e.g., capstans) or devices housed therein to facilitate longitudinal movement (translation) of the drive cables 408a-d within the lumen 410. Selective actuation of the drive cables 408a-d causes corresponding drive cables 408a-d to translate longitudinally within the lumen 410 and thereby cause pivoting movement (articulation) of the end effector 204. Moving a given drive cable 408a-d applies tension (i.e., pull force) to the given drive cable 408a-d in a proximal direction, which causes the given drive cable 408a-d to translate and thereby cause the end effector 204 to move (articulate).

The drive cables 408a-d each extend longitudinally through the first, second, and third linkages 402a-c. In some embodiments, each linkage 402a-c may define four, equidistantly-spaced apertures 412 (only two labeled) configured to guide the drive cables 408a-d through the wrist 206. The apertures 412 of each linkage 402a-c coaxially align when the end effector 204 is in the unarticulated position.

The distal end of each drive cable 408a-d may terminate at the distal linkage 402a, thus operatively coupling each drive cable 408a-d to the end effector 204 and, more particularly, to the lower jaw 212. The distal end of each drive cable 408a-d may be enlarged to facilitate fixed attachment thereof to the end effector 204. In some embodiments, as illustrated, the distal end of each drive cable 408a-d may include a ball crimp 413 (only one shown).

The jaws 210, 212 may be moved between the closed and open positions by pivoting the upper jaw 210 relative to the lower jaw 212. In the illustrated embodiment, the upper jaw 210 may be rotatably coupled (mounted) to the lower jaw 212 at a jaw axle 414. A third pivot axis $P_3$ extends through the jaw axle 414 and is generally perpendicular (orthogonal) to the first pivot axis $P_1$ and parallel to the second pivot axis $P_2$. In this embodiment, the lower jaw 212 remains stationary as the upper jaw 210 pivots about the third pivot axis $P_3$. In other embodiments, the end effector 204 may be designed such that the upper jaw 210 remains stationary as the lower jaw 212 pivots about the third pivot axis $P_3$, without departing from the scope of the disclosure.

A central pulley 416 (partially visible) may be mounted to the jaw axle 414 and receive a jaw cable 418 that may be actuated to selectively open and close the jaws 210, 212. Similar to the drive cables 408a-d, the jaw cable 418 extends longitudinally within the lumen 410 of the shaft 202 and passes through the wrist 206. The jaw cable 418 may form part of the cable driven motion system described herein and, therefore, may extend proximally from the end effector 204 to the drive housing 208 (FIG. 2). The jaw cable 418 may comprise a single line or wire looped around the central pulley 416 and opposing first and second ends 420a and 420b of the jaw cable 418 extend proximally to the drive housing 208. Actuation of corresponding drive inputs will cooperatively cause tension or slack in the jaw cable 418 and thereby cause the upper jaw 210 to rotate about the third pivot axis $P_3$ between the open and closed positions. More specifically, a tensile load assumed on the first end 420a of the jaw cable 418 may operate to close the jaws 210, 212, and a tensile load assumed on the second end 420b of the jaw cable 418 may operate to open the jaws 210, 212. Consequently, the first end 420a of the jaw cable 418 may alternately be referred to as the "closure cable" and the second end 420b of the jaw cable 418 may alternately be referred to as the "open cable."

In some embodiments, an electrical conductor 422 may supply electrical energy to the end effector 204 and, more particularly, to an electrode 424 included in the end effector 204. The electrical conductor 422 extends longitudinally within the lumen 410, through the wrist 206, and terminates at the electrode 424. In some embodiments, the electrical conductor 422 may comprise a wire, but may alternatively comprise a rigid or semi-rigid shaft, rod, or strip (ribbon) made of a conductive material. The electrical conductor 422 may be partially covered with an insulative covering (overmold) made of a non-conductive material. Using the electrical conductor 422 and the electrode 424, the end effector 204 may be configured for monopolar or bipolar operation.

In the illustrated embodiment, the end effector 204 comprises a combination tissue grasper and vessel sealer that includes a cutting element 426 (mostly occluded), alternately referred to as a "knife" or "blade." The cutting element 426 is aligned with and configured to traverse a guide track 428 defined longitudinally in one or both of the upper and lower jaws 210, 212. The cutting element 426 may be operatively coupled to the distal end of a drive rod 430 that extends longitudinally within the lumen 410 and passes through the wrist 206. Longitudinal movement (translation) of the drive rod 430 correspondingly moves the cutting element 426 within the guide track(s) 428. Similar to the drive and jaw cables 408a-d, 418, the drive rod 430 may form part of the cable driven motion system and, therefore, may extend proximally from the cutting element 426 to the drive housing 208 (FIG. 2). Selective actuation of a corresponding drive input will cause the drive rod 430 to move distally or proximally within the lumen 410, and correspondingly move the cutting element 426 in the same direction.

Figure 5:
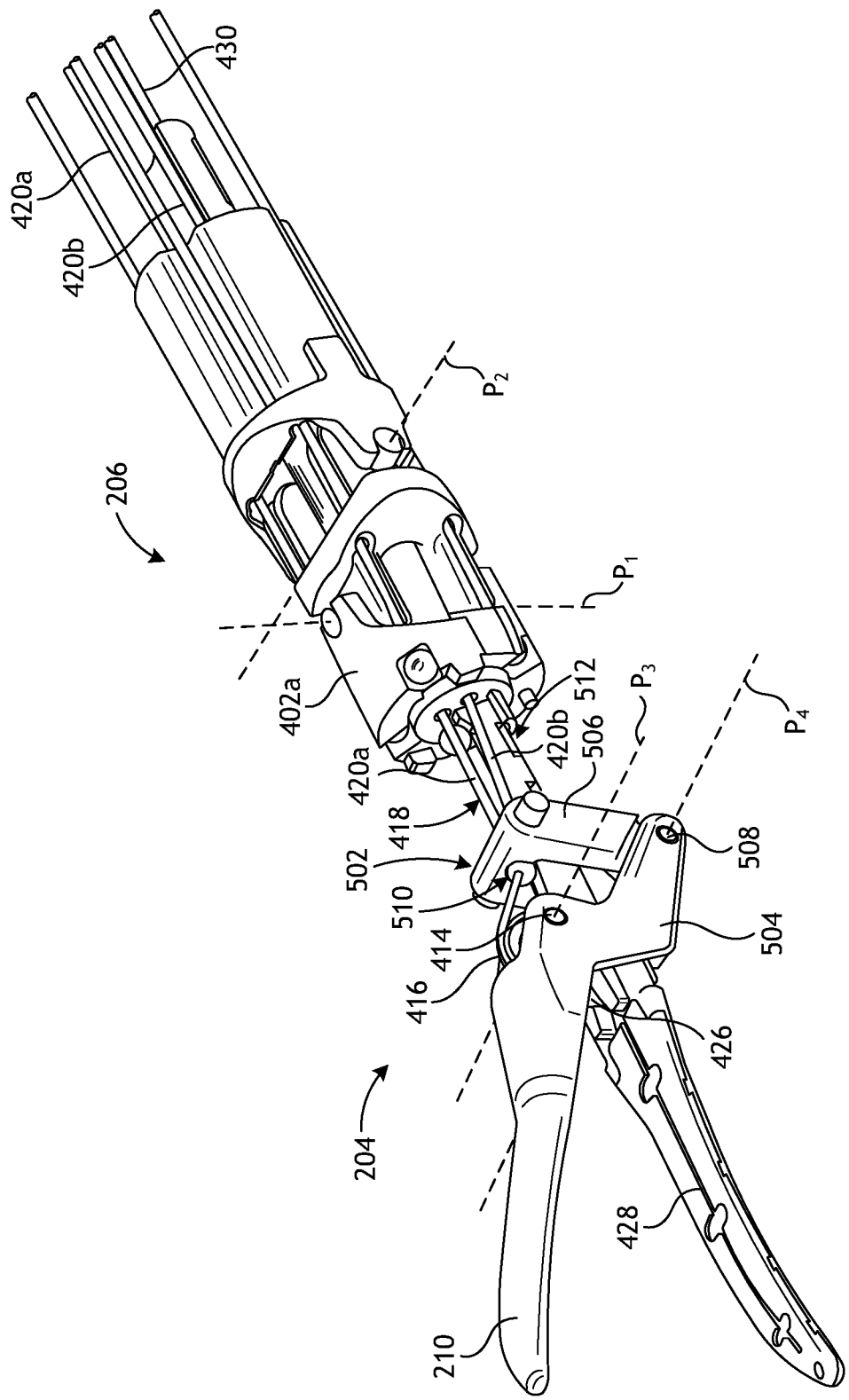
FIG. 5 is an isometric side view of the end effector of FIG. 4 in an open position, according to one or more embodiments.

FIG. 5 is an isometric side view of the end effector 204 in an open position, according to one or more embodiments. More particularly, FIG. 5 depicts the upper jaw 210 pivoted to the open position, and the lower jaw 212 (FIG. 4) is omitted to enable viewing of the internal components of the end effector 204. As illustrated, the end effector 204 includes a pivot link 502 operatively coupled to the upper jaw 210. More specifically, the upper jaw 210 provides or otherwise defines one or more legs 504 (one shown, one occluded) that are pivotably coupled to a corresponding one or more legs 506 (one shown, one occluded) of the pivot link 502 at a pivot axle 508. A fourth pivot axis $P_4$ extends through the pivot axle 508 and may be generally perpendicular (orthogonal) to the first pivot axis $P_1$ and parallel to the second and third pivot axes $P_2$, $P_3$.

The central pulley 416 (mostly occluded) is rotatably supported on the jaw axle 414, and the jaw cable 418 loops around the central pulley 416 and the opposing ends 420a,b of the jaw cable 418 extend proximally through the wrist 206. The jaw cable 418 may be operatively coupled to the pivot link 502 such that movement (i.e., longitudinal translation) of the jaw cable 418 correspondingly moves the pivot link 502. For example, a cable anchor 510 may be secured to or otherwise form part of one proximally extending end 420a,b of the jaw cable 418 and may help operatively couple the jaw cable 418 to the pivot link 502.

To move the jaws 210, 212 to the open position, the jaw cable 418 may be actuated to move the pivot link 502 distally, which may be done, for example, by pulling proximally on the second end 420b of the jaw cable 418 (i.e., the "open cable"). As the pivot link 502 moves distally, the legs 506 of the pivot link 502 act on the legs 504 of the upper jaw 210 at the pivot axle 508 and forces the legs 504 downward in rotation about the fourth pivot axis $P_4$. Downward movement of the legs 504 correspondingly causes the upper jaw 210 to pivot about the third pivot axis $P_3$. As it pivots about the third pivot axis $P_3$, the upper jaw 210 is moved to the open position.

To move the upper jaw 210 back to the closed position, the jaw cable 418 may be actuated to move the pivot link 502 proximally, which may be done by pulling proximally on the first end 420a of the jaw cable 418 (i.e., the "closure cable"). This causes the pivot link 502 to pull upward on the legs 504 of the upper jaw 210 in rotation about the fourth pivot axis $P_4$, and upward movement of the legs 504 correspondingly causes the upper jaw 210 to pivot about the third pivot axis $P_3$ and moves the upper jaw 210 to the closed position.

Figure 6A:
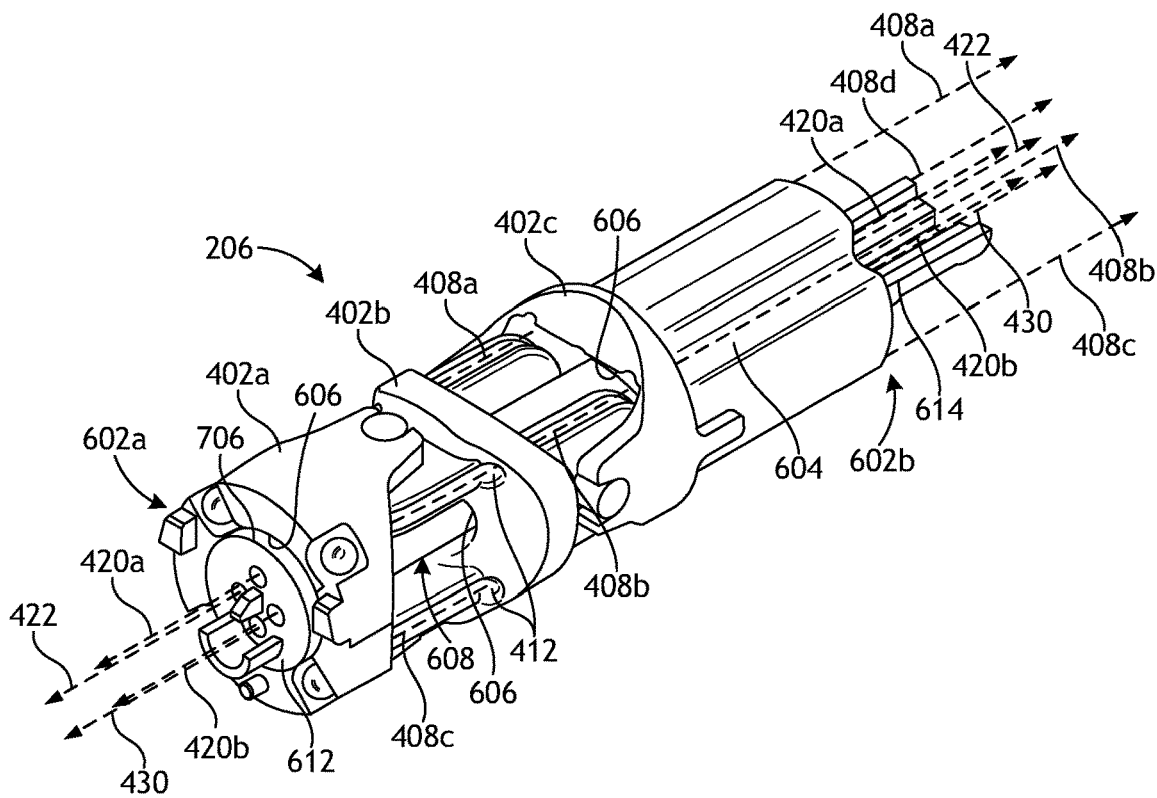
FIGS. 6A and 6B are enlarged isometric front and back views, respectively, of the wrist of FIGS. 4 and 5, according to one or more embodiments.
Figure 6B:
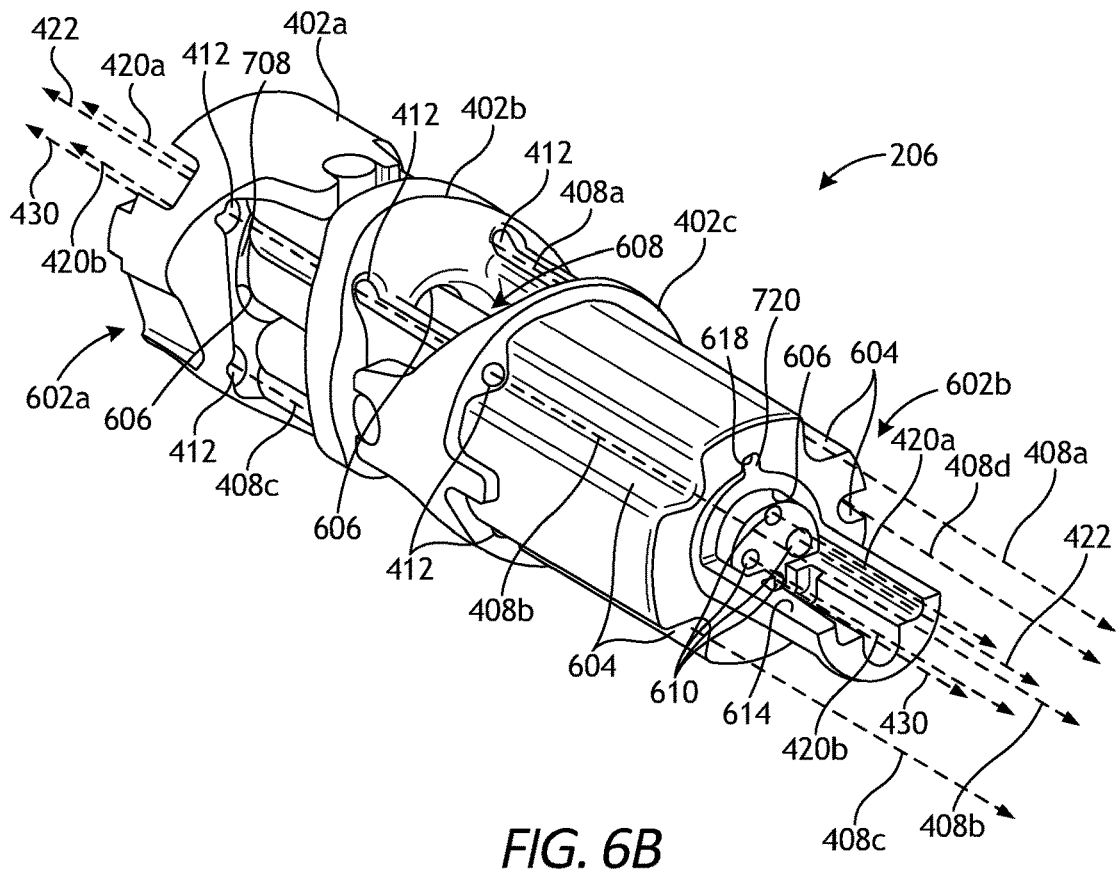

FIGS. 6A and 6B are enlarged isometric front and back views, respectively, of the wrist 206, according to one or more embodiments. The wrist 206 has a first or "distal" end 602a and a second or "proximal" end 602b opposite the distal end 602a. The distal linkage 402a is positioned at the distal end 602a, the proximal linkage 402c is positioned at the proximal end 602b, and the intermediate linkage 402b interposes and operatively couples the distal and proximal linkages 402a,c. However, embodiments are contemplated herein where the intermediate linkage 402b is omitted and the distal and proximal linkages 402a,c are alternatively directly coupled at a common axle.

For simplicity, the drive cables 408a-d, the electrical conductor 422, the first and second ends 420a,b of the jaw cable 418 (FIGS. 4 and 5), and the drive rod 430 are each depicted in FIGS. 6A-6B as dashed lines. The drive cables 408a-d pass through portions (e.g., apertures 412) of the wrist 206 and terminate at the distal linkage 402a. The proximal linkage 402c may provide or otherwise define longitudinal grooves 604 that accommodate the drive cables 408a-d, and each groove 604 may receive a corresponding one of the drive cables 408a-d. The grooves 604 may be aligned with the corresponding apertures 412 defined by the proximal linkage 402c.

The wrist 206 provides or defines a central channel 606 that extends between the distal and proximal ends 602a,b. In embodiments where the wrist 206 includes the distal, intermediate, and proximal linkages 402a-c, corresponding portions of the central channel 606 may be cooperatively and successively defined by each linkage 402a-c. However, in embodiments where the wrist 206 includes only the distal and proximal linkages 402a,c, the central channel 606 may be defined cooperatively and successively by only the distal and proximal linkages 402a,c. The portions of the central channel 606 defined by each linkage 402a-c may coaxially align when the wrist 206 is non-articulated, but move out of axial alignment when the wrist 206 is moved in articulation.

The wrist 206 may further include a flexible member 608 positionable within the central channel 606 and extending at least partially between the first and second ends 602a-b of the wrist 206. As best seen in FIG. 6B, the flexible member 608 may provide or otherwise define one or more conduits 610 (four shown) that extend through the entire length of the flexible member 608. Consequently, the flexible member 608 may alternatively be referred to as a "multilumen" or a "multilumen element." The conduits 610 may be configured to receive the electrical conductor 422, the first and second ends 420a,b of the jaw cable 418 (FIGS. 4 and 5), and the drive rod 430, collectively referred to herein as "central actuation members." Accordingly, the central actuation members may penetrate the wrist 206 by extending through the conduits 610 of the flexible member 608.

In some embodiments, as illustrated, the conduits 610 may exhibit a circular cross-sectional shape, but could alternatively exhibit other cross-sectional shapes, such as polygonal, oval, or ovoid, without departing from the scope of the disclosure. Moreover, one or more of the conduits 610 may be lined with a material that helps mitigate abrasion and friction, such as nylon, silicone, nitinol, etc. Furthermore, the size (diameter) of the conduits 610 may vary, depending on the application. Those skilled in the art will readily appreciate that the shape, material, and size of the conduits 610 may be altered or otherwise customized consistent with known industry practices, without departing from the scope of the disclosure.

The flexible member 608 may be operatively coupled to the distal linkage 402a at its distal end, but may be free to move relative to the proximal linkage 402c at its proximal end. In some embodiments, for example, the wrist 206 may include a distal adapter 612 (FIG. 6A) and a proximal adapter 614 (FIG. 6B). The distal adapter 612 may operatively couple the flexible member 608 to the distal linkage 402a, and the proximal adapter 612 may be configured to support the flexible member 608 in sliding engagement with the proximal linkage 402c. In at least one embodiment, however, the proximal adapter 612 may be omitted and the flexible member 608 may directly contact the proximal linkage 402c in sliding engagement.

Figure 7A:
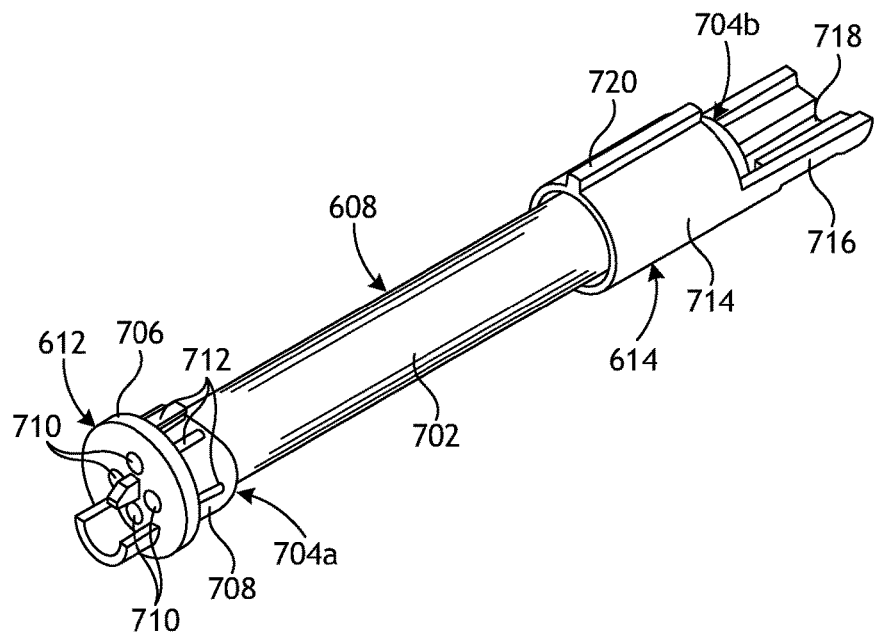
FIGS. 7A and 7B are isometric and exploded views, respectively, of the flexible member and the distal and proximal adapters of FIGS. 6A-6B, according to one or more embodiments.
Figure 7B:
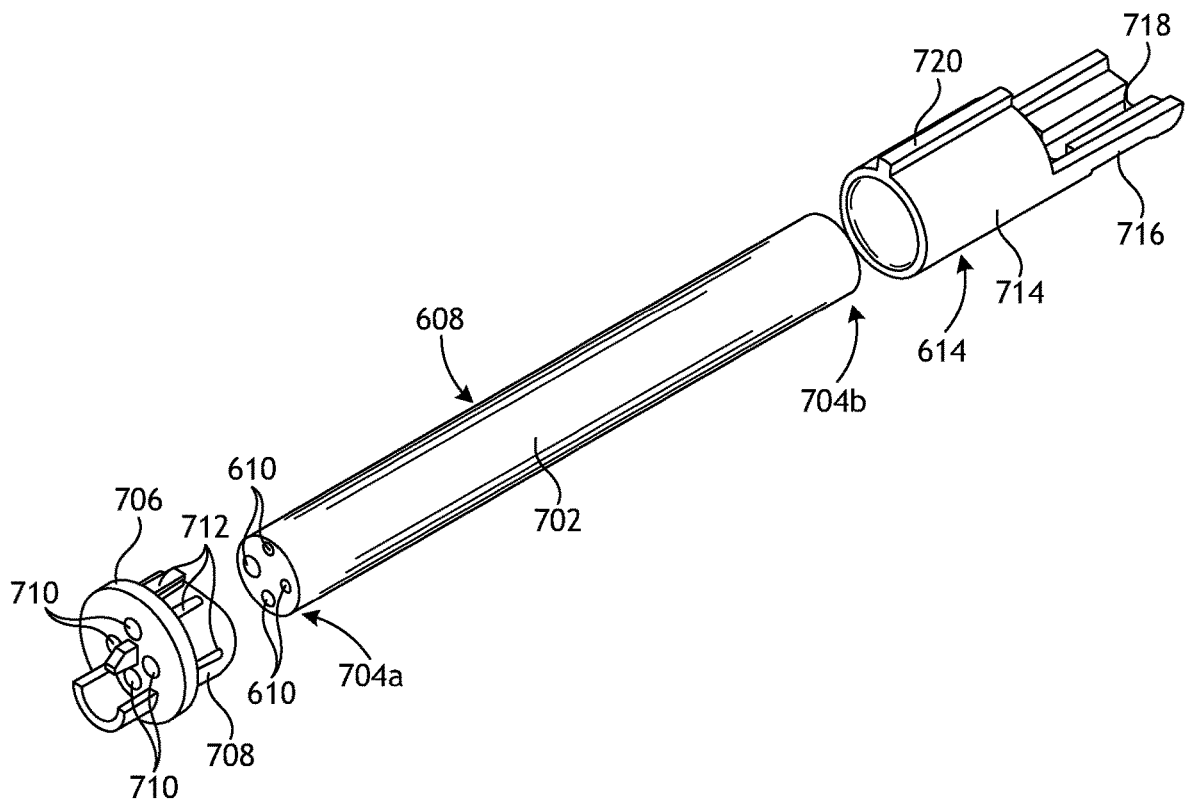

FIGS. 7A and 7B are isometric and exploded views, respectively, of the flexible member 608 and the distal and proximal adapters 612, 614, according to one or more embodiments. As illustrated, the flexible member 608 may comprise a generally cylindrical body 702 having a first or "distal" end 704a and a second or "proximal" end 704b opposite the distal end 704a. In some embodiments, as illustrated, the body 702 may exhibit a substantially circular cross-section, but may alternatively exhibit other cross-sectional shapes, such as polygonal (e.g., triangular, rectangular, etc.), polygonal with rounded corners, oval, ovoid, or any combination thereof, without departing from the scope of the disclosure.

The flexible member 608 may be made of any flexible or semi-flexible material that allows the flexible member 608 to flex or bend when the wrist 206 (FIGS. 6A-6B) articulates. The material for the flexible member 608 may also exhibit low friction characteristics or may otherwise be lubricious, which may prove advantageous in minimizing friction caused by the central actuation members (e.g., the electrical conductor 422, the first and second ends 420a,b of the jaw cable 418, and the drive rod 430 of FIGS. 6A-6B) extending through the conduits 610. Furthermore, the material for the flexible member 608 may also exhibit good wear characteristics so the central actuation members do not inadvertently cut through the corresponding conduits 610 following repeated use. The diameter or size of each conduit 610 may be large enough to enable the central actuation members to move therein without substantive obstruction (friction), but small enough to support the central actuation members for longitudinal movement.

Suitable materials for the flexible member 608 include, but are not limited to, polytetrafluoroethylene (PTFE or TEFLON®), silicone, nylon, a thermoplastic polyurethane (TPU, e.g., CARBOTHANE™, PELLETHANE®, TECO-BAX™), a thermoplastic elastomer (TPE, e.g., PEBAX®), or any combination thereof. In at least one embodiment, the flexible member 608 may comprise an extrusion or may otherwise be manufactured through an extrusion process. In other embodiments, the flexible member 608 may be printed through an additive manufacturing process (e.g., 3D printing).

The distal adapter 612 may be made of a rigid or semi-rigid material including, but not limited to, a plastic, a metal, a composite material, and any combination thereof. Example materials for the distal adapter 612 include, but are not limited to, polyetherimide, polycarbonate, polystyrene, and nylon. In some embodiments, as illustrated, the distal adapter 612 may provide or otherwise define a radial shoulder 706 and a flange 708 that extends from the radial shoulder 706. The flange 708 may be sized to receive the distal end 704a of the flexible member 608. In other embodiments, however, the flange 708 may be omitted and the distal adapter 612 may nonetheless be coupled to the flexible member 608.

The distal adapter 612 may be coupled (fixed) to the distal end 704a of the flexible member 608 via a variety of attachment means. Suitable attachment means include, but are not limited to, bonding (e.g., an adhesive), welding (e.g., sonic or ultrasonic welding), overmolding the distal adapter 612 onto the distal end 704*a*, an interference or shrink fit, or any combination thereof.

The distal adapter 612 may define one or more or apertures 710 (four shown) configured to co-axially align with the conduits 610 of the flexible member 608. Accordingly, the central actuation members extending through the flexible member 608 (e.g., the electrical conductor 422, the first and second ends 420*a,b* of the jaw cable 418, and the drive rod 430 of FIGS. 6A-6B) may each exit the flexible member 608 and extend through the distal adapter 612 at the apertures 710.

In some embodiments, the distal adapter 612 may provide one or more features 712 configured to mate with one or more corresponding features of the distal linkage 402*a* (FIGS. 6A-6B). In the illustrated embodiment, the features 712 are defined on the flange 708, but could alternatively be defined on any other portion of the distal adapter 612, without departing from the scope of the disclosure. Mating the features 712 of the distal adapter 612 with the corresponding features of the distal linkage 402*a* may help rotationally fix the distal end 704*a* of the flexible member 608 at the distal end 602*a* (FIGS. 6A-6B) of the wrist 206 (FIGS. 6A-6B).

The proximal adapter 614 may be made of a rigid or semi-rigid material including, but not limited to, a plastic, a metal, a composite material, or any combination thereof. Example materials for the proximal adapter 614 include, but are not limited to, polyetherimide, polycarbonate, polystyrene, and nylon. The proximal adapter 614 may provide a generally annular body 714 sized to receive the proximal end 704*b* of the flexible member 608. In some embodiments, the proximal end 704*b* may extend entirely through the annular body 714, but may alternatively extend only partially therethrough.

The proximal adapter 614 may be coupled (fixed) to the proximal end 704*b* of the flexible member 608 via a variety of attachment means. Suitable attachment means include, but are not limited to, bonding (e.g., an adhesive), welding (e.g., sonic or ultrasonic welding), overmolding the proximal adapter 614 onto the proximal end 704*b*, an interference or shrink fit, or any combination thereof.

In some embodiments, a flange 716 may extend proximally from the body 714 of the proximal adapter 614 and may provide or define a groove 718 co-axially alignable with one of the conduits 610. The groove 718 may be sized to receive one of the central actuation members, such as the drive rod 430 (FIGS. 5 and 6A-6B), which may prove advantageous in helping to prevent buckling of the drive rod 430 during operation.

The proximal adapter 614 may provide one or more features 720 matable with one or more corresponding features provided by the proximal linkage 402*c* (FIGS. 6A-6B). As discussed in more detail below, the feature 720 may comprise a longitudinal rib that may be configured to mate with a longitudinal channel of the proximal linkage 402*c*.

Referring again to FIGS. 6A-6B, in some embodiments, the distal adapter 612 may be partially received within the central channel 606 defined in the distal linkage 402*a*. More specifically, the flange 708 (see FIG. 6B) of the distal adapter 612 may extend into the central channel 606 until the radial shoulder 706 (see FIG. 6A) of the distal adapter 612 engages the distal end 602*a* of the wrist 206 and, more particularly, the distal linkage 402*a*. In some embodiments, one or more features (not shown) may be defined on the inner radial surface of the central channel 606 at the distal linkage 402*a* and configured to mate with the features 712 (FIGS. 7A-7B) of the distal adapter 612. Mating these features may help rotationally fix the distal adapter 612 relative to the distal end 602*a* (FIGS. 6A-6B) of the wrist 206 (FIGS. 6A-6B).

The distal adapter 612 may be arranged to interpose the lower jaw 212 (FIG. 4) and the distal linkage 402*a* within the assembly of the end effector 204 (FIGS. 4-5), thus restraining (trapping) the distal adapter 612 between the lower jaw 212 and the distal linkage 402*a*. Since the distal adapter 612 may be fixed to the distal end 704*a* (FIGS. 7A-7B) of the flexible member 608, restraining (trapping) the distal adapter 612 between the lower jaw 212 and the distal linkage 402*a* may correspondingly fix the flexible member 608 in place at the distal end 602*a* of the wrist 206.

Referring specifically to FIG. 6B, the proximal linkage 402*c* may provide or define a feature 618 sized and otherwise configured to receive (mate with) the feature 720 provided by the proximal adapter 614. In the illustrated embodiment, the feature 618 comprises a longitudinal channel, and the feature 720 comprises a longitudinal rib matable with the longitudinal channel. Mating the features 618, 720 may help rotationally fix the flexible member 608 to the proximal linkage 402*c*, but also allows the flexible member 608 to move longitudinally relative to the proximal linkage 402*c*. For example, as the wrist 206 articulates, the feature 720 of the proximal adapter 614 may slide relative to the feature 618 of the proximal linkage 402*c*. In some embodiments, however, the proximal adapter 614 may be omitted and the feature 720 may alternatively be provided by the flexible member 608, without departing from the scope of the disclosure. In other embodiments, the flexible member 608 may be molded or otherwise formed in a shape that lends itself to be rotationally fixed to the proximal linkage 402*c*, such as a square or "D" shape.

In example operation of the wrist 206, the drive cables 408*a*-*d* are selectively actuated to articulate the wrist 206. As the wrist 206 articulates, the flexible member 608 correspondingly bends or flexes, and the central actuation members (e.g., the electrical conductor 422, the first and second ends 420*a,b* of the jaw cable 418, and the drive rod 430) will correspondingly move in the direction of articulation and thereby lengthen or shorten, depending on the bend direction. Extending the central actuation members through the conduits 610 of the flexible member 608 creates a defined and predictable pathway for each central actuation member.

Undesirable movement at the tip of the end effector 204 (FIG. 2) can occur when a high closure force is applied to the closure cable (e.g., the first end 420*a* of the jaw cable 418) to clamp the jaws 210, 212 onto tissue, or when tension is applied to the open cable (e.g., the second end 420*b* of the jaw cable 418) to open the jaws 210, 212 against tissue. This jaw tip motion is generated by slight off-center positional offsets of the closure cable (or the open cable) at one or both of the articulation joints (i.e., the first and second pivot axes $P_1$, $P_2$ of FIGS. 4-5) during movement. This creates an unbalancing moment that can cause the jaws 210, 212 to move abruptly or "dive" in the direction of the imbalance. This "tip dive" is unexpected and undesirable when clamping critical structures. According to embodiments of the present disclosure, a pair of laterally-offset roller supports may be included (installed) in the wrist 206 at each articulation joint to support and prevent the closure and open cables from deviating below, across, or past the pivot axes $P_1$, $P_2$ during actuation, which can help mitigate tip dive during closing and opening the jaws 210, 212.

Figure 8A:
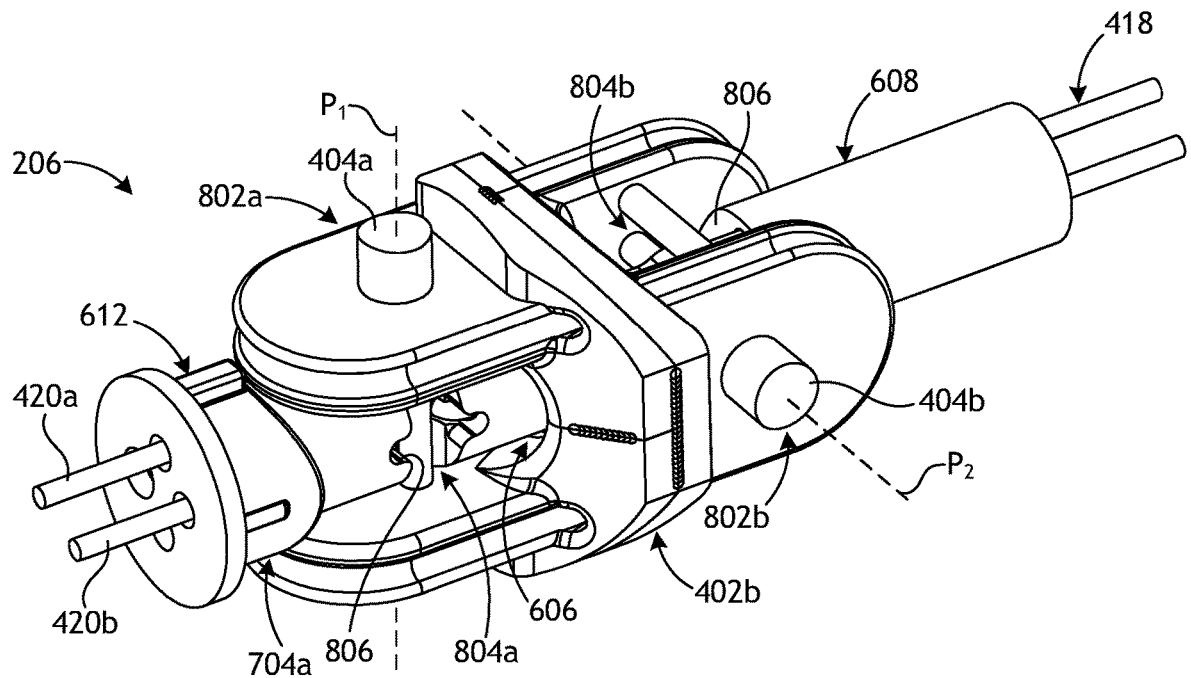
FIGS. 8A and 8B are front and back isometric views, respectively, of an example embodiment of the wrist of FIGS. 4, 5, and 6A-6B that may incorporate one or more principles of the present disclosure.
Figure 8B:
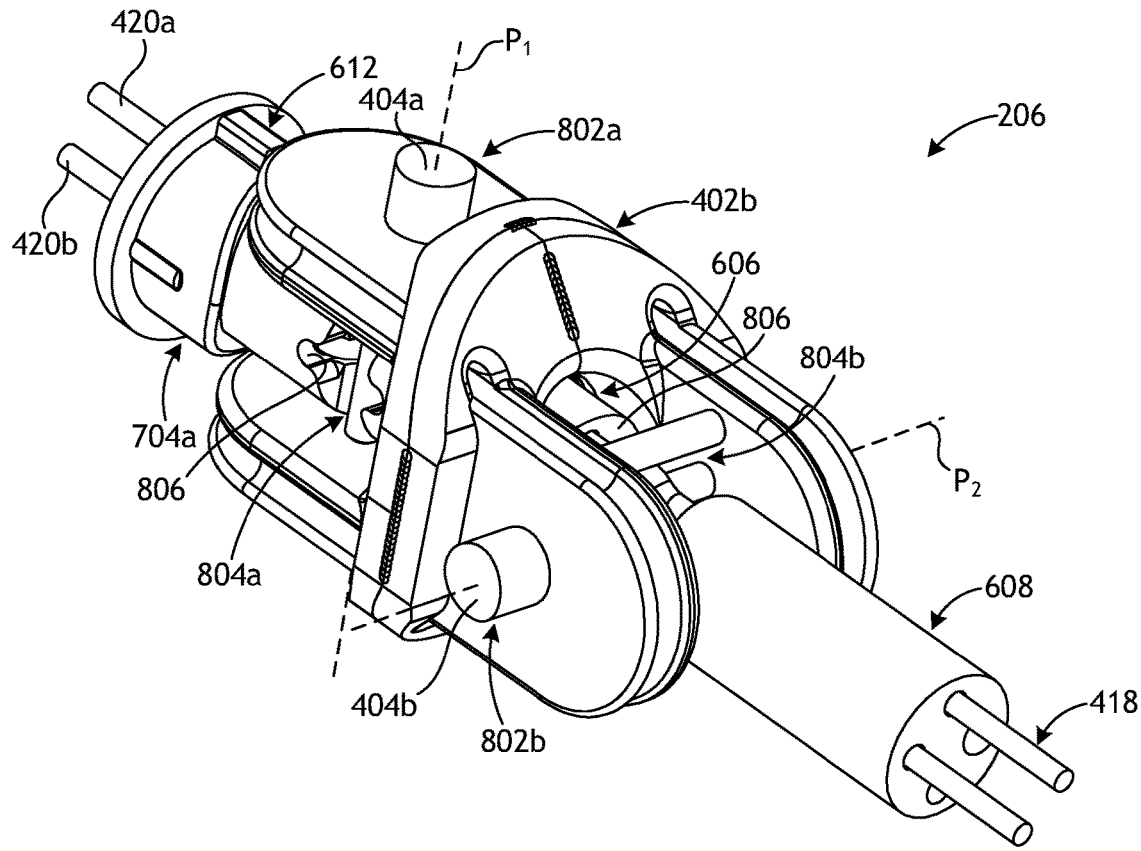

FIGS. 8A and 8B are front and back isometric views, respectively, of an example embodiment of the wrist 206 that may incorporate one or more principles of the present disclosure. For simplicity, the drive cables 408a-d (FIGS. 4-5), the electrical conductor 422 (FIGS. 4-5), and the drive rod 430 (FIGS. 4-5) are each omitted in FIGS. 8A-8B, but would otherwise be included in a full (complete) assembly of the wrist 206. Moreover, the distal linkage 402a (FIGS. 4, 5, and 6A-6B) is omitted, but would otherwise be rotatably coupled to the intermediate linkage 402b at the first axle 404a to provide a first articulation joint 802a, and the proximal linkage 402c (FIGS. 4, 5, and 6A-6B) is omitted, but would otherwise be rotatably coupled to the intermediate linkage 402b at the second axle 404b to provide a second articulation joint 802b.

The first pivot axis $P_1$ extends through the first articulation joint 802a and facilitates "yaw" movement (articulation) of the end effector 204 (FIGS. 2, 4, and 5), and the second pivot axis $P_2$ extends through the second articulation joint 802b and facilitates "pitch" movement (articulation) of the end effector 204. In some embodiments, the wrist 206 may alternatively include only the intermediate linkage and one of the distal or proximal linkages 402a,c. In such embodiments, the wrist 206 would only have one articulation joint capable of facilitating either "yaw" or "pitch" movement, depending on the orientation of the associated pivot axis.

The flexible member 608 (FIGS. 6A-6B and 7A-7B) is extendable through the central channel 606 of the wrist 206 and, in the illustrated embodiment, the proximal adapter 612 is coupled to the distal end 704a of the flexible member 608. Moreover, the first and second ends 420a,b of the jaw cable 418 are depicted as extending through the flexible member 608. The first and second ends 420a,b of the jaw cable 418 will be referred to below as the "closure" and "open" cables 420a,b respectively.

In the illustrated embodiment, the wrist 206 also includes a first pair of roller supports 804a (only one of the two visible) arranged at the first articulation joint 802a, and a second pair of roller supports 804b arranged at the second articulation joint 802b. One or more reliefs or cutouts 806 may be defined in the flexible member 608 to accommodate the roller supports 804a,b and to help eliminate stress concentrations at the first and second articulation joints 802a,b during articulation. While the present embodiment includes a pair of roller supports 804a,b at each articulation joint 802a,b, it is contemplated herein to employ only one pair of roller supports 804a,b at a corresponding one of the articulation joints 802a,b, without departing from the scope of the disclosure.

The first pair of roller supports 804a are laterally offset from each other and extend generally parallel to each other and the first pivot axis $P_1$. Similarly, the second pair of roller supports 804b are laterally offset from each other and extend parallel to each other and the second pivot axis $P_2$. Accordingly, the first and second pairs of roller supports 804a,b are substantially perpendicular (orthogonal) to one another.

In assembling the wrist 206, the closure and open cables 420a,b are routed (extended) through corresponding gaps defined between each pair of roller supports 804a,b. The roller supports 804a,b help support the closure and open cables 420a,b during articulation at the articulation joints 802a,b, thus preventing the closure and open cables 420a,b from deviating (migrating) past the first and second pivot axes $P_1$, $P_2$ when actuating the end effector 204 (FIGS. 2, 4, and 5), which could otherwise result in undesirable tip dive at the end effector 204.

More particularly, the wrist 206 is articulable in pitch motion at the second articulation joint 802b and otherwise moved about the second pivot axis $P_2$. As the closure cable 420a tightens to close the jaws 210, 212 (FIGS. 2, 4, and 5) when the wrist 206 is articulated in pitch, the closure cable 420a will tend to find the shortest path through the second articulation joint 802b. The second pair of roller supports 804b, however, helps support the closure cable 420a at the second articulation joint 802b and prevents the centerline of the closure cable 420a from deviating below (past) the second pivot axis $P_2$ during clamping, which will mitigate tip dive at the end effector 204 (FIGS. 2, 4, and 5). Similarly, when the wrist 206 is articulated in yaw motion at the first articulation joint 802a and the open cable 420b tightens to open the jaws 210, 212, the open cable 420b will tend to find the shortest path through the first articulation joint 802a. The first pair of roller supports 804a, however, helps to support the open cable 420b at the first articulation joint 802a and thereby prevents the centerline of the open cable 420b from deviating across (past) the first pivot axis $P_1$ during opening, which will also mitigate tip dive at the end effector 204.

Figure 9A:
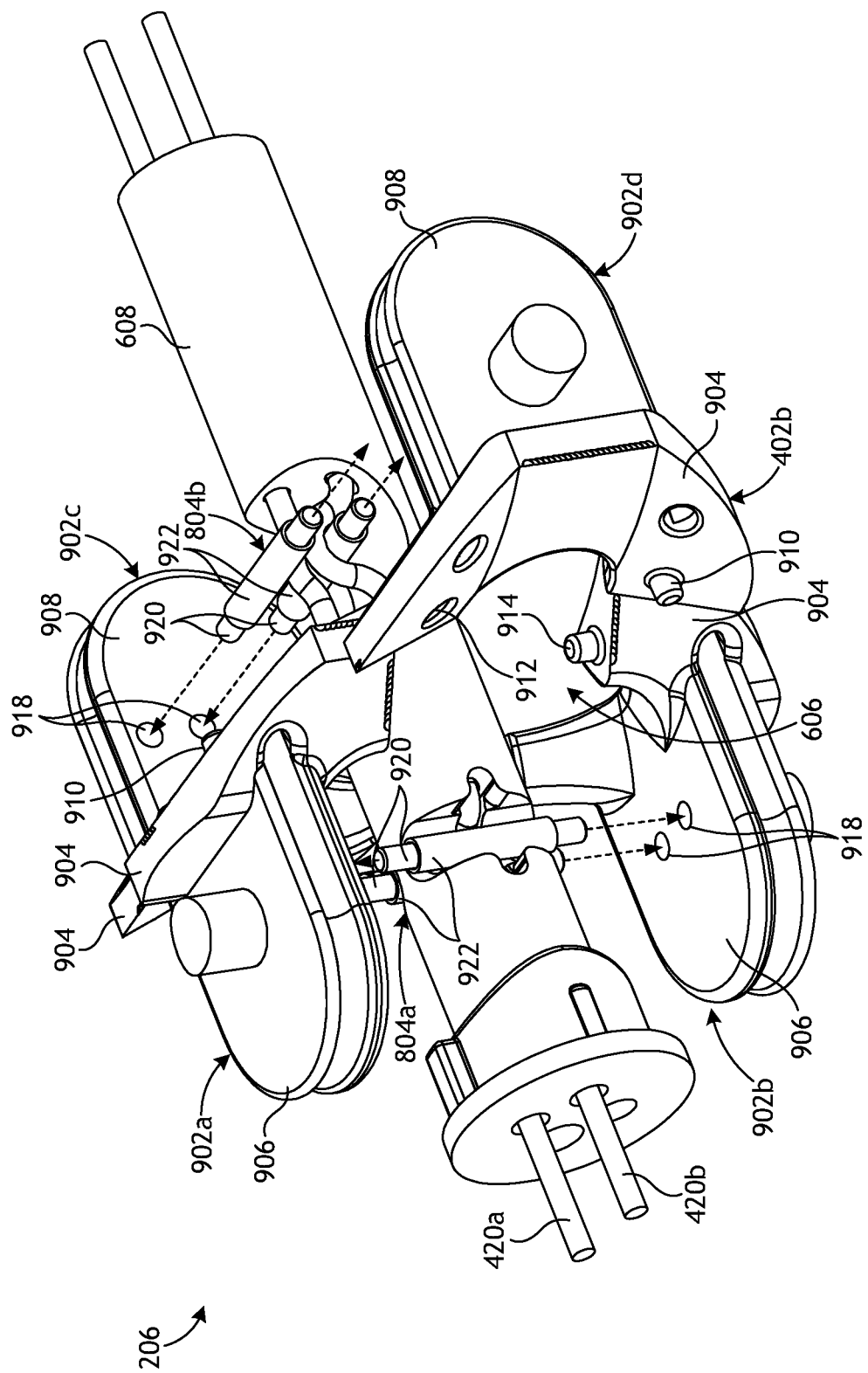
FIGS. 9A and 9B are exploded, front and back isometric views, respectively, of the wrist of FIGS. 8A-8B, according to one or more embodiments.
Figure 9B:
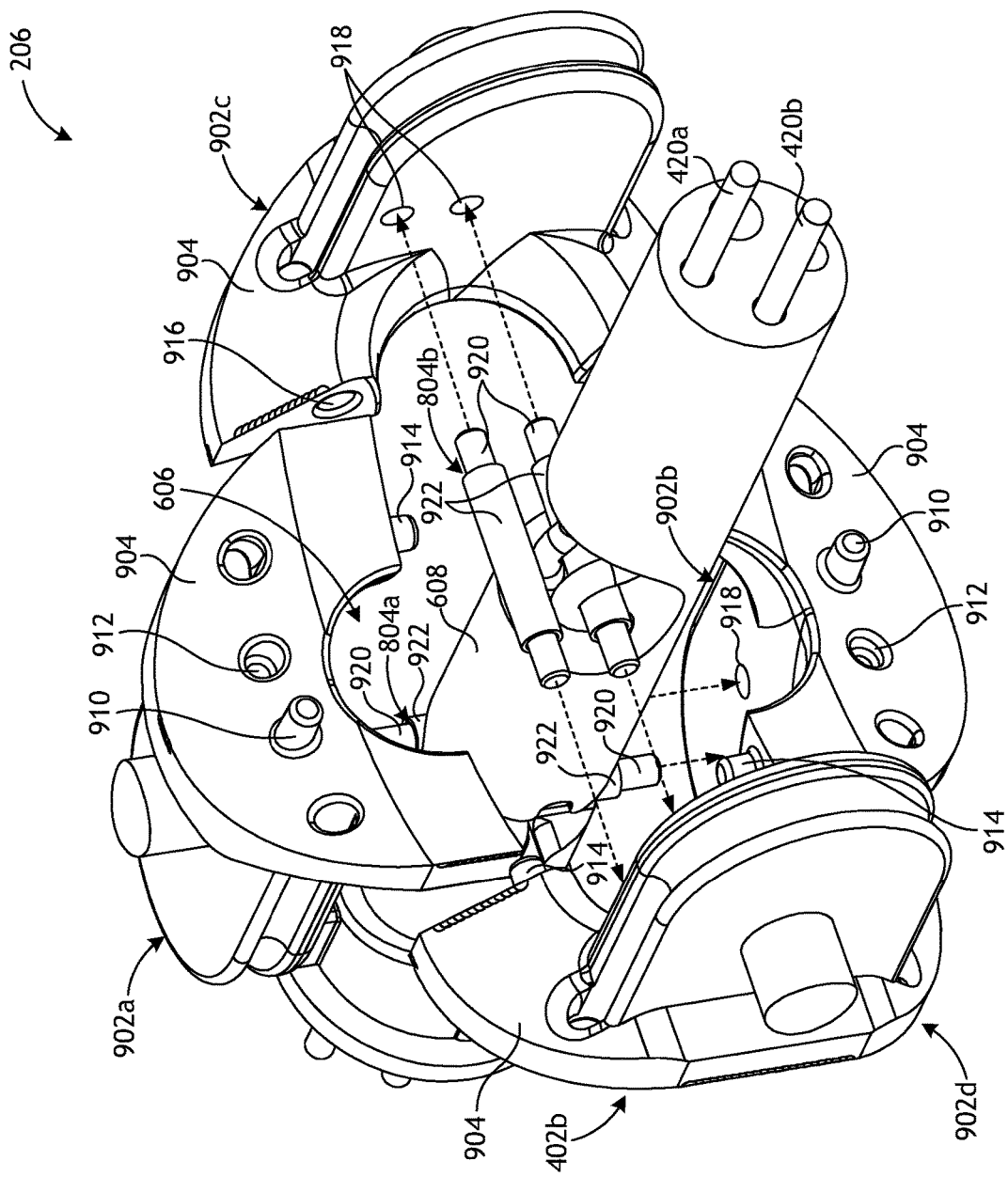

FIGS. 9A and 9B are exploded, front and back isometric views, respectively, of the wrist 206 of FIGS. 8A-8B, according to one or more embodiments. In the illustrated embodiment, the intermediate linkage 402b may be made of two or more pieces or component parts, shown as a first piece 902a, a second piece 902b, a third piece 902c, and a fourth piece 902d. While four pieces 902a-d are depicted in FIGS. 9A-9B, the intermediate linkage 402b may alternatively comprise two, three, or more than four pieces or parts, without departing from the scope of the disclosure.

The pieces 902a-d may be matable to form the intermediate linkage 402b and thereby help define a portion of the central channel 606 through which the flexible member 608 extends. In some embodiments, two or more of the pieces 902a-d may be mirror images of each other, but oriented differently to enable a mated engagement. Having the intermediate linkage 402b made up of two or more pieces 902a-d may help enable (facilitate) assembly of the roller supports 804a,b in the intermediate linkage 402b.

The pieces 902a-d may be made of any rigid or semi-rigid material including, but not limited to, a plastic, a metal, a composite material, an elastomer, or any combination thereof. In at least one embodiment, one or more of the pieces 902a-d may be made of a metal and manufactured through metal injection molding with some post machining on critical surfaces and/or pivoting locations. In some embodiments, the pieces 902a-d may be mated and then permanently secured together to form the intermediate linkage 402b. Suitable securing methods include, but are not limited to, welding (e.g., laser, metal, sonic, ultrasonic, etc.), an adhesive attachment, an interference fit between opposing pins and apertures (as described below), forcible deformation of opposing pins and apertures (e.g., similar to rivet coupling), crimping or swaging deformable materials, or any combination thereof. In other embodiments, however, securing the pieces 902a-d together may not be required since once the distal and proximal linkages 402a,c (FIGS. 4, 5, and 6A-6B) are rotatably coupled to the intermediate linkage 402b, the pieces 902a-d will be trapped in place by the distal and proximal linkages 402a,c.

Each piece 902a-d may provide or otherwise define a generally arcuate body 904, and when the pieces 902a-d are mated, the combined arcuate bodies 904 align to form the central channel 606. In the illustrated embodiment, the first and second pieces 902a,b may each provide a distally extending lobe 906 extending from the corresponding body 904, and the third and fourth pieces 902c,d may each provide a proximally extending lobe 908 extending from the corresponding body 904. When the pieces 902a-d are mated to form the intermediate linkage 402b, the distally extending lobes 906 will be parallel and laterally offset from one another and the proximally extending lobes 908 will be parallel and laterally offset from one another. Moreover, when the pieces 902a-d are mated to form the intermediate linkage 402b, the distally extending lobes 906 will extend orthogonal (i.e., angularly offset by 90°) to the proximally extending lobes 908, which allows the intermediate linkage 402b to facilitate both "yaw" and "pitch" articulation of the end effector 204 (FIGS. 2, 4, and 5).

In some embodiments, one or more of the arcuate bodies 904 of the pieces 902a-d may include or otherwise define an axially-extending pin 910 configured mate with a corresponding hole 912 defined in an opposing arcuate body 904 of an adjacent piece 902a-d. In at least one embodiment, each arcuate body 904 provides a corresponding axially-extending pin 910 configured mate with a corresponding hole 912 defined in an opposing arcuate body 904. Alternatively, or in addition thereto, one or more of the arcuate bodies 904 may include or otherwise define a radially-extending pin 914 configured mate with a corresponding hole 916 defined in an opposing arcuate body 904 of an adjacent piece 902a-d. In at least one embodiment, each arcuate body 904 provides a corresponding radially-extending pin 914 matable with a corresponding hole 916 defined in an opposing arcuate body 904.

The pins 910, 914 and the corresponding holes 912, 916 may operate as locating features (e.g., self-aligning features) that help angularly and axially align the pieces 902a-d for proper mating engagement. In some embodiments, one or more of the pins 910, 914 may be tapered to enable easier locating and mating engagement with the corresponding holes 912, 916, respectively.

The first pair of roller supports 804a extend between the distally extending lobes 906, and the second pair of roller supports 804b extend between the proximally extending lobes 908. When the pieces 902a-d are mated to form the intermediate linkage 402b, the ends of each roller support 804a,b may be received within corresponding apertures 918 defined in the adjacent lobes 906, 908. The roller supports 804a,b will be secured to the intermediate linkage 402b at the corresponding lobes 906, 908 upon mating the pieces 902a-d.

In some embodiments, each roller support 804a,b may comprise a roller 920 and a sleeve 922 disposed about the roller 920. Material properties (e.g., hardness, lubricity, etc.) of the roller 920 and the sleeve 922 of each roller support 804a,b may be optimized to improve wear against each other, the opposing lobes 906, 908, and the closure and open cables 420a,b. The rollers 920, for example, may be made of any substantially rigid material including, but not limited to, a plastic (polymer), a metal (e.g., tungsten carbide), a composite material, a ceramic (e.g., toughened, reinforced, etc.), or any combination thereof. In at least one embodiment, one or more of the rollers 902 may be made of a tungsten rhenium alloy (e.g., W-25), which has an elastic modulus that is about two times greater than that of steel. Example non-metal materials for the rollers 920 include, but are not limited to, polyetherimide (e.g., ULTEM®), polycarbonate, polystyrene, polyether ether ketone (PEEK), and nylon.

The sleeves 922 may be generally cylindrical structures arranged about the outer circumference of the corresponding roller 902. The closure and open cables 420a,b may be engageable against the outer surface of the sleeves 922 during operation and, in at least one embodiment, axial translation of the closure and open cables 420a,b may urge the underlying engaged sleeves 922 to rotate relative to the corresponding roller 902. The sleeves 922 may be made of a low-friction (lubricious) material that minimizes galling against the closure and open cables 420a,b and allows the sleeves 922 to rotate with little resistance. Suitable materials for the sleeves 922 include, but are not limited to, PEEK, nylon, polytetrafluoroethylene (PTFE), perfluoropolyether (PFPE) lubricated polymer, polyoxymethylene (POM), or any combination thereof. In some embodiments, the inner surface of the sleeves 922 and/or the outer surface of the rollers 920 may be polished and/or include a lubricant, which may help reduce friction and galling as the sleeves 922 rotate during operation, and thus increase device mission life.

As indicated above, the first pair of roller supports 804a are laterally offset from each other, and the second pair of roller supports 804b are laterally offset from each other. The closure and open cables 420a,b extend through the corresponding gaps defined between each pair of roller supports 804a,b, and the roller supports 804a,b help support the closure and open cables 420a,b during articulation. More particularly, when the wrist 206 is articulated in pitch motion at the second articulation joint 802b (FIGS. 8A-8B) and the closure cable 420a simultaneously tightens to close the jaws 210, 212 (FIGS. 2, 4, and 5), the closure cable 420a will tend to find the shortest path through the second articulation joint 802b. The second pair of roller supports 804b, however, is positioned to engage and support the closure cable 420a at the second articulation joint 802b and thereby prevents the centerline of the closure cable 420a from deviating below (past, beyond) the second pivot axis $P_2$ (FIGS. 8A-8B) during clamping. Consequently, this will help mitigate tip dive at the end effector 204 (FIGS. 2, 4, and 5).

Similarly, when the wrist 206 is articulated in yaw motion at the first articulation joint 802a (FIGS. 8A-8B) and the open cable 420b simultaneously tightens to open the jaws 210, 212 (FIGS. 2, 4, and 5), the open cable 420b will tend to find the shortest path through the first articulation joint 802a. The first pair of roller supports 804a, however, is positioned to engage and support the open cable 420b at the first articulation joint 802a and thereby prevents the centerline of the open cable 420b from deviating past (beyond) the first pivot axis $P_1$ (FIGS. 8A-8B). Consequently, this will also help mitigate tip dive at the end effector 204 (FIGS. 2, 4, and 5).

Embodiments disclosed herein include:

A. An articulable wrist for an end effector includes a first linkage rotatably coupled to a second linkage at a first articulation joint, a flexible member extending at least partially through a central channel cooperatively defined by the first and second linkages, a first pair of roller supports arranged at the first articulation joint and laterally offset from each other, each roller support extending parallel to a first pivot axis extending through the first articulation joint, and a drive cable extending through a first axially-extending conduit defined in the flexible member and through a gap defined between the first pair of roller supports, wherein the drive cable is supported at the first articulation joint by the first pair of roller supports during articulation and the first pair of roller supports prevents a centerline of the drive cable from moving past the first pivot axis during actuation of the end effector.

B. A surgical tool includes a drive housing, an elongate shaft that extends from the drive housing, an end effector arranged at an end of the elongate shaft, an articulable wrist that interposes the end effector and the elongate shaft, the articulable wrist including: a first linkage rotatably coupled to a second linkage at a first articulation joint, a flexible member extending at least partially through a central channel cooperatively defined by the first and second linkages, a first pair of roller supports arranged at the first articulation joint and laterally offset from each other, each roller support extending parallel to a first pivot axis extending through the first articulation joint, and a drive cable extending from the drive housing to the end effector, the drive cable further extending through a first axially-extending conduit defined in the flexible member and through a gap defined between the first pair of roller supports. The drive cable is supported at the first articulation joint by the first pair of roller supports during articulation of the end effector and the first pair of roller supports prevents a centerline of the drive cable from moving past the first pivot axis during actuation of the end effector.

C. A method of operating a surgical tool includes positioning the surgical tool adjacent a patient for operation, the surgical tool including a drive housing, an elongate shaft that extends from the drive housing, an end effector arranged at an end of the elongate shaft, and a wrist that interposes the end effector and the elongate shaft and includes a first linkage rotatably coupled to a second linkage at a first articulation joint, a flexible member extending at least partially through a central channel cooperatively defined by the first and second linkages, a first pair of roller supports arranged at the first articulation joint and laterally offset from each other, each roller support extending parallel to a first pivot axis extending through the first articulation joint, and a drive cable extending from the drive housing to the end effector, the drive cable further extending through a first axially-extending conduit defined in the flexible member and through a gap defined between the first pair of roller supports. The method further includes articulating the wrist and simultaneously bending the flexible member within the central channel, and supporting the drive cable at the first articulation joint with the first pair of roller supports during articulation and thereby preventing a centerline of the drive cable from moving past the first pivot axis during actuation of the end effector.

Each of embodiments A, B, and C may have one or more of the following additional elements in any combination: Element 1: wherein the second linkage comprises a pair of distally extending lobes laterally offset from each other, and apertures defined in each distally extending lobe to receive corresponding ends of each roller support. Element 2: wherein each roller support comprises a roller, and a cylindrical sleeve disposed about an outer circumference roller and engageable with the drive cable during articulation. Element 3: wherein the roller is made of a rigid material selected from the group consisting of a plastic, a metal, a composite material, a ceramic, and any combination thereof. Element 4: wherein the sleeve is made of a low-friction material selected from the group consisting of polyether ether ketone, nylon, polytetrafluoroethylene, perfluoropolyether lubricated polymer, polyoxymethylene, and any combination thereof. Element 5: wherein the sleeve is rotatable relative to the roller. Element 6: further comprising a third linkage rotatably coupled to the second linkage at a second articulation joint and cooperatively defining the central channel with the first and second linkages, a second pair of roller supports arranged at the second articulation joint and laterally offset from each other, each roller support of the second pair of roller supports extending parallel to a second pivot axis extending through the first articulation joint, and an second drive cable extending through a second axially-extending conduit defined in the flexible member and through a gap defined between the second pair of roller supports, wherein the second drive cable is supported at the second articulation joint by the second pair of roller supports during articulation and the second pair of roller supports prevents a centerline of the second drive cable from moving past the second pivot axis during actuation of the end effector. Element 7: further wherein one or more reliefs are defined in the flexible member at the first and second articulation joints to accommodate the first and second pairs of roller supports and help eliminate stress concentrations at the first and second articulation joints during articulation. Element 8: wherein the second linkage comprises a first piece providing a first distally extending lobe, a second piece providing a second distally extending lobe laterally offset from the first distally-extending lobe when the first and second pieces are mated, wherein the first pair of roller supports extends between the first and second distally extending lobes, a third piece providing a first proximally extending lobe, and a fourth piece providing a second proximally extending lobe laterally offset from the first proximally extending lobe when the third and fourth pieces are mated, wherein the second pair of roller supports extends between the first and second distally extending lobes. Element 9: wherein one or more of the first, second, third, and fourth pieces are made of a rigid or semi-rigid material selected from the group consisting of a plastic, a metal, a composite material, an elastomer, a ceramic, and any combination thereof. Element 10: wherein the first, second, third, and fourth pieces are permanently secured together. Element 11: wherein the first and second distally extending lobes are angularly offset from the first and second proximally extending lobes by 90°. Element 12: wherein the first, second, third, and fourth pieces each provide a corresponding arcuate body, and one or more of the arcuate bodies includes at least one of an axially-extending pin matable with a corresponding hole defined in an opposing arcuate body of an adjacent one of the first, second, third, or fourth pieces, and a radially-extending pin matable with a corresponding hole defined in an opposing arcuate body of an adjacent one of the first, second, third, or fourth pieces. Element 13: wherein at least one of the axially-extending pin and the radially-extending pin is tapered.

Element 14: wherein each roller support comprises a roller, and a cylindrical sleeve disposed about an outer circumference roller and engageable with the closure cable during articulation. Element 15: further comprising a third linkage rotatably coupled to the second linkage at a second articulation joint and cooperatively defining the central channel with the first and second linkages, a second pair of roller supports arranged at the second articulation joint and laterally offset from each other, each roller support of the second pair of roller supports extending parallel to a second pivot axis extending through the first articulation joint, and an second drive cable extending from the drive housing to the end effector and further extending through a second axially-extending conduit defined in the flexible member and through a gap defined between the second pair of roller supports, wherein the second drive cable is supported at the second articulation joint by the second pair of roller supports during articulation of the end effector and the second pair of roller supports prevents a centerline of the second drive cable from moving past the second pivot axis during actuation of the end effector. Element 16: wherein the second linkage comprises a first piece providing a first distally extending lobe, a second piece providing a second distally extending lobe laterally offset from the first distally-extending lobe when the first and second pieces are mated, wherein the first pair of roller supports extends between the first and second distally extending lobes, a third piece providing a first proximally extending lobe, and a fourth piece providing a second proximally extending lobe laterally offset from the first proximally extending lobe when the third and fourth pieces are mated, wherein the second pair of roller supports extends between the first and second distally extending lobes.

Element 17: wherein the wrist further includes a third linkage rotatably coupled to the second linkage at a second articulation joint and cooperatively defining the central channel with the first and second linkages, a second pair of roller supports arranged at the second articulation joint and laterally offset from each other, each roller support of the second pair of roller supports extending parallel to a second pivot axis extending through the first articulation joint, an second drive cable extending from the drive housing to the end effector and further extending through a second axially-extending conduit defined in the flexible member and through a gap defined between the second pair of roller supports, the method further comprising supporting the second cable at the second articulation joint with the second pair of roller supports during articulation and thereby preventing a centerline of the second drive cable from moving past the second pivot axis during actuation of the end effector.

By way of non-limiting example, exemplary combinations applicable to A, B, and C include: Element 2 with Element 3; Element 2 with Element 4; Element 2 with Element 5; Element 6 with Element 7; Element 6 with Element 8; Element 8 with Element 9; Element 8 with Element 10; Element 8 with Element 11; Element 8 with Element 12; Element 12 with Element 13; and Element 15 with Element 16.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. An articulable wrist for an end effector, comprising:
   a first linkage rotatably coupled to a second linkage at a first articulation joint;
   a flexible member extending at least partially through a central channel cooperatively defined by the first and second linkages;
   a first pair of roller supports arranged at the first articulation joint and laterally offset from each other, each roller support extending parallel to but eccentric from a first pivot axis extending through the first articulation joint; and
   a drive cable extending through a first axially-extending conduit defined in the flexible member and through a gap defined between the first pair of roller supports, wherein the drive cable is supported at the first articulation joint by the first pair of roller supports during articulation and the first pair of roller supports prevents a centerline of the drive cable from moving past the first pivot axis during actuation of the end effector.

2. The articulable wrist of claim 1, wherein the second linkage comprises:
   a pair of distally extending lobes laterally offset from each other; and
   apertures defined in each distally extending lobe to receive corresponding ends of each roller support.

3. The articulable wrist of claim 1, wherein each roller support comprises:
   a roller; and
   a cylindrical sleeve disposed about an outer circumference of the roller and engageable with the drive cable during articulation.

4. The articulable wrist of claim 3, wherein the roller is made of a rigid material selected from the group consisting of a plastic, a metal, a composite material, a ceramic, and any combination thereof.

5. The articulable wrist of claim 3, wherein the sleeve is made of a low-friction material selected from the group consisting of polyether ether ketone, nylon, polytetrafluoroethylene, perfluoropolyether lubricated polymer, polyoxymethylene, and any combination thereof.

6. The articulable wrist of claim 1, further comprising:
   a third linkage rotatably coupled to the second linkage at a second articulation joint and cooperatively defining the central channel with the first and second linkages;
   a second pair of roller supports arranged at the second articulation joint and laterally offset from each other, each roller support of the second pair of roller supports extending parallel to a second pivot axis extending through the first articulation joint; and an second drive cable extending through a second axially-extending conduit defined in the flexible member and through a gap defined between the second pair of roller supports, wherein the second drive cable is supported at the second articulation joint by the second pair of roller supports during articulation and the second pair of roller supports prevents a centerline of the second drive cable from moving past the second pivot axis during actuation of the end effector.

7. The articulable wrist of claim 6, wherein one or more reliefs are defined in the flexible member at the first and second articulation joints to accommodate the first and second pairs of roller supports and help eliminate stress concentrations at the first and second articulation joints during articulation.

8. The articulable wrist of claim 6, wherein the second linkage comprises:
  a first piece providing a first distally extending lobe;
  a second piece providing a second distally extending lobe laterally offset from the first distally-extending lobe when the first and second pieces are mated, wherein the first pair of roller supports extends between the first and second distally extending lobes;
  a third piece providing a first proximally extending lobe; and
  a fourth piece providing a second proximally extending lobe laterally offset from the first proximally extending lobe when the third and fourth pieces are mated, wherein the second pair of roller supports extends between the first and second distally extending lobes.

9. The articulable wrist of claim 8, wherein one or more of the first, second, third, and fourth pieces are made of a rigid or semi-rigid material selected from the group consisting of a plastic, a metal, a composite material, an elastomer, a ceramic, and any combination thereof.

10. The articulable wrist of claim 8, wherein the first, second, third, and fourth pieces are permanently secured together.

11. The articulable wrist of claim 8, wherein the first and second distally extending lobes are angularly offset from the first and second proximally extending lobes by 90°.

12. The articulable wrist of claim 8, wherein the first, second, third, and fourth pieces each provide a corresponding arcuate body, and one or more of the arcuate bodies includes at least one of:
  an axially-extending pin matable with a corresponding hole defined in an opposing arcuate body of an adjacent one of the first, second, third, or fourth pieces; and
  a radially-extending pin matable with a corresponding hole defined in an opposing arcuate body of an adjacent one of the first, second, third, or fourth pieces.

13. The articulable wrist of claim 12, wherein at least one of the axially-extending pin and the radially-extending pin is tapered.

14. The articulable wrist of claim 1, wherein one or more reliefs are defined in the flexible member at the first articulation joint to accommodate the first pair of roller supports.

15. A surgical tool, comprising:
  a drive housing;
  an elongate shaft that extends from the drive housing;
  an end effector arranged at an end of the elongate shaft; and
  an articulable wrist that interposes the end effector and the elongate shaft, the articulable wrist including:
    a first linkage rotatably coupled to a second linkage at a first articulation joint;
    a flexible member extending at least partially through a central channel cooperatively defined by the first and second linkages;
    a first pair of roller supports arranged at the first articulation joint and laterally offset from each other, each roller support extending parallel to but eccentric from a first pivot axis extending through the first articulation joint; and
    a drive cable extending from the drive housing to the end effector, the drive cable further extending through a first axially-extending conduit defined in the flexible member and through a gap defined between the first pair of roller supports,
  wherein the drive cable is supported at the first articulation joint by the first pair of roller supports during articulation of the end effector and the first pair of roller supports prevents a centerline of the drive cable from moving past the first pivot axis during actuation of the end effector.

16. The surgical tool of claim 15, wherein each roller support comprises:
  a roller; and
  a cylindrical sleeve disposed about an outer circumference roller and engageable with the closure cable during articulation.

17. The surgical tool of claim 15, further comprising:
  a third linkage rotatably coupled to the second linkage at a second articulation joint and cooperatively defining the central channel with the first and second linkages;
  a second pair of roller supports arranged at the second articulation joint and laterally offset from each other, each roller support of the second pair of roller supports extending parallel to a second pivot axis extending through the first articulation joint; and
  an second drive cable extending from the drive housing to the end effector and further extending through a second axially-extending conduit defined in the flexible member and through a gap defined between the second pair of roller supports,
  wherein the second drive cable is supported at the second articulation joint by the second pair of roller supports during articulation of the end effector and the second pair of roller supports prevents a centerline of the second drive cable from moving past the second pivot axis during actuation of the end effector.

18. The surgical tool of claim 17, wherein the second linkage comprises:
  a first piece providing a first distally extending lobe;
  a second piece providing a second distally extending lobe laterally offset from the first distally-extending lobe when the first and second pieces are mated, wherein the first pair of roller supports extends between the first and second distally extending lobes;
  a third piece providing a first proximally extending lobe; and
  a fourth piece providing a second proximally extending lobe laterally offset from the first proximally extending lobe when the third and fourth pieces are mated, wherein the second pair of roller supports extends between the first and second distally extending lobes.

19. A method of operating a surgical tool, comprising:
  positioning the surgical tool adjacent a patient for operation, the surgical tool including a drive housing, an elongate shaft that extends from the drive housing, an end effector arranged at an end of the elongate shaft, and a wrist that interposes the end effector and the elongate shaft and includes:
a first linkage rotatably coupled to a second linkage at a first articulation joint;
a flexible member extending at least partially through a central channel cooperatively defined by the first and second linkages;
a first pair of roller supports arranged at the first articulation joint and laterally offset from each other, each roller support extending parallel to but eccentric from a first pivot axis extending through the first articulation joint; and
a drive cable extending from the drive housing to the end effector, the drive cable further extending through a first axially-extending conduit defined in the flexible member and through a gap defined between the first pair of roller supports,
articulating the wrist and simultaneously bending the flexible member within the central channel; and
supporting the drive cable at the first articulation joint with the first pair of roller supports during articulation and thereby preventing a centerline of the drive cable from moving past the first pivot axis during actuation of the end effector.

20. The method of claim 19, wherein the wrist further includes:
a third linkage rotatably coupled to the second linkage at a second articulation joint and cooperatively defining the central channel with the first and second linkages;
a second pair of roller supports arranged at the second articulation joint and laterally offset from each other, each roller support of the second pair of roller supports extending parallel to a second pivot axis extending through the first articulation joint;
an second drive cable extending from the drive housing to the end effector and further extending through a second axially-extending conduit defined in the flexible member and through a gap defined between the second pair of roller supports, the method further comprising:
supporting the second cable at the second articulation joint with the second pair of roller supports during articulation and thereby preventing a centerline of the second drive cable from moving past the second pivot axis during actuation of the end effector.

* * * * *